United States Patent [19]

Toki et al.

[11] Patent Number: 5,360,806

[45] Date of Patent: Nov. 1, 1994

[54] AMIDE COMPOUNDS AND THEIR SALTS AND PESTICIDAL COMPOSITIONS CONTAINING THEM

[75] Inventors: Tadaaki Toki; Toru Koyanagi; Masayuki Morita; Tetsuo Yoneda; Chiharu Kagimoto; Hiroshi Okada, all of Kusatsu, Japan

[73] Assignee: Ishihara Sangyo Kaisha Ltd., Osaka, Japan

[21] Appl. No.: 95,192

[22] Filed: Jul. 23, 1993

[30] Foreign Application Priority Data

| Jul. 23, 1992 | [JP] | Japan | 4-238804 |
| Feb. 5, 1993 | [JP] | Japan | 5-057668 |
| Mar. 17, 1993 | [JP] | Japan | 5-096428 |

[51] Int. Cl.$^5$ ............ C07D 401/12; C07D 213/82; A01N 43/40
[52] U.S. Cl. ............ 514/318; 514/231.5; 514/255; 514/332; 514/343; 514/355; 546/193; 546/262; 546/281; 546/316; 544/124; 544/360
[58] Field of Search ............ 546/193, 265, 262, 281, 546/636; 544/124, 360; 514/231.5, 255, 318, 332, 343, 355

[56] References Cited

FOREIGN PATENT DOCUMENTS

| 0149324 | 7/1985 | European Pat. Off. . |
| 0185256 | 6/1986 | European Pat. Off. . |
| 63-130583 | 6/1988 | Japan . |
| WO92/12133 | 7/1992 | WIPO . |

OTHER PUBLICATIONS

Chemical Abstracts, vol. 97, Abstract No. 23,598t, p. 695 1982.
Intermediates Catalogue, May 5, 1992, pp. 134 & 321, "Intermediates 92/93".
Chemical Abstracts, vol. 113, 1990, pp. 700–701.
Alam et al., Chemical Abstracts, vol. 97, No. 3, Abstract 23,598t, p. 694, Jul. 19, 1982.

*Primary Examiner*—C. Warren Ivy
*Assistant Examiner*—Zinna N. Davis
*Attorney, Agent, or Firm*—Oblon, Spivak, McClelland, Maier & Neustadt

[57] ABSTRACT

The present invention relates to an amide compound and its salt, process for its production and a pesticidal composition containing it.

The amide compound of the formula (I) or its salt:

wherein the radicals are defined in the claims.

12 Claims, No Drawings

AMIDE COMPOUNDS AND THEIR SALTS AND PESTICIDAL COMPOSITIONS CONTAINING THEM

The present invention relates to amide compounds and their salts, processes for producing them and pesticidal compositions containing them as active ingredients.

Various compounds are known as active ingredients for pesticides. However, their chemical structures are different from the amide compounds of the present invention.

Heretofore, organophosphorus compounds, carbamate compounds and pyrethroid compounds have been used as active ingredients for pesticides such as insecticides. As a result, some insect pests have acquired a resistance to such insecticides in recent years. Therefore, a pesticide which is effective against pests having such a resistance, is desired. Further, research and development have been conducted for a new pesticide which is more effective against insect pests and safer to fish, shellfish and domestic animals or which has a wider pesticidal spectrum.

It is an object of the present invention to provide amide compounds having pesticidal activities, processes for their production and pesticidal compositions containing them.

The present inventors have conducted extensive studies to develop pesticides, and have found that amide compounds having a certain specific chemical structure have excellent pesticidal activities. The present invention has been accomplished on the basis of this discovery.

Thus, the present invention provides an amide compound of the formula (I) or its salt:

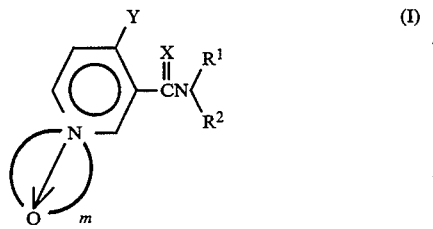

wherein X is an oxygen atom or a sulfur atom, Y is haloalkyl group, each of $R^1$ and $R^2$ which are independent of each other, is a hydrogen atom, an alkyl group which may be substituted, an alkenyl group which may be substituted, an alkynyl group which may be substituted, a cycloalkyl group which may be substituted, $-C(W^1)R^3$, $-S(O)_nR^4$ or $-NHR^5$, or $R^1$ and $R^2$ together form $=C(R^6)R^7$ or together with the adjacent nitrogen atom form a $C_{4-5}$ 5- or 6-member heterocyclic group which may contain a nitrogen atom or an oxygen atom, $R^3$ is an alkyl group which may be substituted, an alkenyl group which may be substituted, an alkynyl group which may be substituted, a cycloalkyl group which may be substituted, an aryl group which may be substituted, an alkoxy group, an alkylthio group or a mono- or di-alkylamino group, $R^4$ is an alkyl group or a dialkylamino group, $R^5$ is an alkyl group or an aryl group, each of $R^6$ and $R^7$ which are independent of each other, is an alkoxy group or an alkylthio group, $W^1$ is an oxygen atom or a sulfur atom, m is 0 or 1, and n is 1 or 2; a process for the production thereof, and a pesticidal composition containing it.

Now, the present invention will be described in detail with reference to the preferred embodiments. In the formula (I), Y is a haloalkyl group such as $CF_3$, $CHF_2$, $CH_2F$, $CF_2Cl$, $CFCl_2$, $CCl_3$, $CH_2CF_3$, $CF_2CF_3$, $CHBr_2$, $CH_2Br$ or the like. Y is preferably a haloalkyl group having 1 to 2 carbon atoms and 1 to 5 halogen atoms, more preferably trifluoromethyl.

The substituent for the alkyl group which may be substituted, the alkenyl group which may be substituted, the alkynyl group which maybe substituted or the cycloalkyl group which may be substituted in the definition of each of $R^1$, $R^2$ and $R^3$ in the formula (I), may, for example, be a halogen atom; alkoxy; alkylthio; trialkylsilyl; phenyl; phenyl substituted by halogen, alkyl, alkoxy, nitro or haloalkyl; phenyl substituted by phenoxy which may be substituted by alkoxy or alkylthio; phenoxy; phenylthio; amino; amino substituted by one or two alkyl; $C_{2-6}$ cyclic amino; morpholino; morpholino substituted by alkyl; 1-piperazinyl; 1-piperazinyl substituted by alkyl, phenyl, pyridyl or trifluoromethylpyridyl; hydroxy; cyano; cycloalkyl; imino; $-C(W^2)R^8$ (wherein $W^2$ is an oxygen atom or a sulfur atom, and $R^8$ is a hydrogen atom, amino, amino substituted by one or two alkyl, alkyl, alkoxy, alkylthio or aryl) or $-OC(W^2)R^9$ (wherein $R^9$ is alkyl or aryl substituted by haloalkyl); or an alkylsulfonyl. When the above substituent is an imino group, it may form an amidino group or an imidate group together with an amino group or an alkoxy group.

The substituent for the alkyl group which may be substituted in the definition of each of $R^1$ and $R^2$, includes, for example, a 4-haloalkyl-3-pyridine carboxamide group, a N-methyl-4-haloalkyl-3-pyridine carboxamide group and a 4-haloalkyl-3-pyridine carboxamide-N-alkylenoxygroup. A chemical structure of the formula (I) containing such a substituent will be represented, for example, by the following formula:

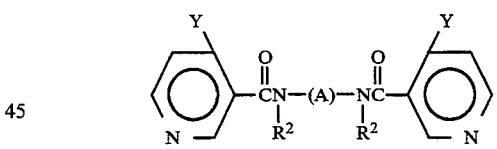

wherein Y and $R^2$ are as defined above, and A is $-(CH_2)_l-$ or $-(CH_2)_q-O-(CH_2)_q-$, l is an integer of from 1 to 4, and q is 1 or 2. Namely, the compound of the formula is a dimer having the compounds of the formula (I) linked by e.g. an alkylene chain. Likewise, the compound of the present invention includes a trimer based on the same concept.

The substituent for the aryl group which may be substituted in the definition for $R^3$ in the formula (I), may, for example, be a halogen atom, alkyl, haloalkyl, alkoxy, haloalkoxy, alkylthio, cycloalkyl, cycloalkoxy, alkoxycarbonyl, alkylcarbonyl, alkylcarbonyloxy, aryl, aryloxy, arylthio, amino, amino substituted by one or two alkyl, cyano, nitro or hydroxy.

In the formula (I), the alkyl group or the alkyl moiety included in $R^1$ or $R^2$ may, for example, be the one having from 1 to 6 carbon atoms, such as a methyl group, an ethyl group, a propyl group, a butyl group, a pentyl group or a hexyl group, and the one having 3 or more carbon atoms may have a linear or branched isomeric structure. The alkenyl group included in $R^1$ or $R^2$ may, for example, be the one having from 2 to 6 carbon atoms such as an ethenyl group, a propenyl group, a butenyl group, a pentenyl group or a hexenyl group, and the one having three or more carbon atoms may have a linear or branched isomeric structure. The alkynyl group included in $R^1$ or $R^2$ may, for example, be the one having from 2 to 6 carbon atoms such as an ethynyl group, a propynyl group, a butynyl group, a pentynyl group or a hexynyl group, and the one having three or more carbon atoms may have a linear or branched isomeric structure. The cycloalkyl group included in $R^1$ or $R^2$ may, for example, be the one having from 3 to 8 carbon atoms, such as a cyclopropyl group, a cyclobutyl group, a cyclopentyl group or a cyclohexyl group.

In the formula (I), the $C_{4-5}$ 5- or 6-member heterocyclic group which may contain a nitrogen atom or an oxygen atom, formed by $R^1$ and $R^2$ together with the adjacent nitrogen atom, may, for example, be a morpholino group, a pyrrolidino group, a piperidino group, a 1-imidazolidinyl group, a 2-cyanoimino-3-methyl-1-imidazolidinyl group, a 1-piperazinyl group or a 4-methyl-1-piperazinyl group.

The aryl group used in the definition for the formula (I), may, for example, be a phenyl group, a thienyl group, a furanyl group, a pyridyl group, a naphthyl group, a benzothienyl group, a benzofuranyl group or a quinolinyl group.

The compound of the formula (I) may form a salt with an acidic substance or a basic substance. The salt with an acidic substance may be an inorganic salt such as a hydrochloride, a hydrobromide, a phosphate, a sulfate or a nitrate. The salt with a basic substance may be a salt of an inorganic or organic base, such as a sodium salt, a potassium salt, a calcium salt, an ammonium salt or a dimethylamine salt.

The amide compound or its salt of the present invention is preferably as follows:

(1) A compound of the formula (I) or its salt, wherein X is an oxygen atom.

(2) A compound of the formula (I) or its salt, wherein each of $R^1$ and $R^2$ which are independent of each other, is a hydrogen atom, an alkyl group which may be substituted or —$C(W^1)R^3$, or $R^1$ and $R^2$ together form =$C(R^6)R^7$, $W^1$ is an oxygen atom or a sulfur atom, $R^3$ is an alkyl group which may be substituted, an aryl group which may be substituted, or an alkoxy group, and each of $R^6$ and $R^7$ which are independent of each other, is an alkoxy group or an alkylthio group.

More preferred is a compound of the formula (I) or its salt, wherein X is an oxygen atom, each of $R^1$ and $R^2$ which are independent of each other, is a hydrogen atom, an alkyl group, an alkoxyalkyl group, an alkylaminoalkyl group, a $C_{2-6}$ cyclic aminoalkyl group, a hydroxyalkyl group, a cyanoalkyl group, a thiocarbamoylalkyl group, an alkylcarbonyloxyalkyl group, an alkylcarbonyl group, an arylcarbonyl group, a trifluoromethyl-substituted arylcarbonyl group, an alkoxythiocarbonyl group or an alkoxycarbonyl group, or $R^1$ and $R^2$ together form =$C(R^6)R^7$, and $R^6$ and $R^7$ are an alkoxy group and an alkylthio group, respectively.

Specific examples of preferred compounds are as follows:

4-trifluoromethyl-3-pyridinecarboxamide, N-cyanomethyl-4-trifluoromethyl-3-pyridine carboxamide, N-thiocarbamoylmethyl-4-trifluoromethyl-3-pyridine carboxamide, N-ethoxymethyl-4-trifluoromethyl-3-pyridine carboxamide, N-isopropylaminomethyl-4-trifluoromethyl-3-pyridine carboxamide, N-cyanomethyl-N,N-bis(4-trifluoromethylnicotinoyl)amine, N-acetyl-N-cyanomethyl-4-trifluoromethyl-3-pyridine carboxamide, N-cyanomethyl-N-methyl-4-trifluoromethylpyridine-3-carboxamide, O-methyl N-(4-trifluoromethylnicotinoyl)thiocarbamate, N-methyl-4-trifluoromethylpyridine-3-carboxamide, N-(N',N'-dimethylaminomethyl)-4-trifluoromethylpyridine-3carboxamide, N-(1-piperidinyl)-4-trifluoromethylpyridine-3-carboxamide, N-cyanomethyl N-(4-trifluoromethylnicotinoyl)aminomethylpivarate, O,S-dimethyl N-(4-trifluoromethylnicotinoyl)iminoformate, N-hydroxymethyl-4-trifluoromethyl-3-pyridine carboxamide, N-acetyl-4-trifluoromethyl-3-pyridine carboxamide or methyl N-(4-trifluoromethylnicotinoyl)carbamate, or a 1-oxide thereof.

The compound of the formula (I) or its salt can be produced, for example, by the following method (A):

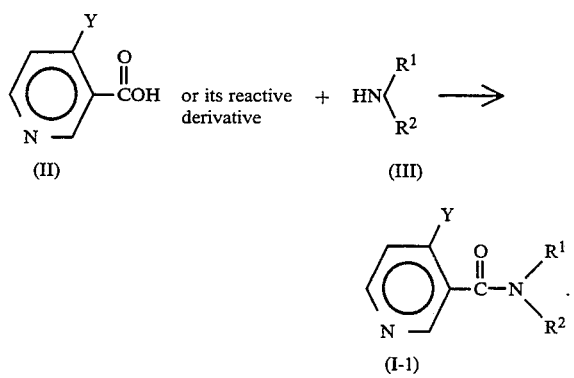

In the above formulas, Y, $R^1$ and $R^2$ are as defined above.

The reactive derivative of 4-haloalkylpyridine-3carboxylic acid of the formula (II) may, for example, be an acid halide, an ester or an acid anhydride.

The above reaction is conducted usually in the presence of a solvent, if necessary, in the presence of a base. The solvent may, for example, be an aromatic hydrocarbon such as benzene or toluene; an ether such as diethyl ether or tetrahydrofuran; a halogenated hydrocarbon such as methylene chloride or chloroform; or an aprotic polar solvent such as acetonitrile, dimethylformamide or pyridine. These solvents may be used alone or in combination as a mixture. The base may, for example, be a tertiary amine such as trimethylamine, triethylamine or pyridine; an alkali metal hydroxide such as sodium hydroxide or potassium hydroxide; an alkali metal carbonate such as sodium carbonate or potassium carbonate; or an alkali metal alkoxide such as sodium methoxide or sodium ethoxide. When the reactant is 4-haloalkylpyridine-3-carboxylic acid, it is common to use a condensation agent such as dicyclohexylcarbodiimide, N,N'-carbonyldiimidazole or 1-ethyl-3-(3-dimethylaminopropyl)carbodiimide.

The reaction temperature for the above reaction is usually from —50° C. to +100° C. However, when the reactive derivative is an acid halide or an acid anhydride, the temperature is preferably from 0° to 30° C., and when the reactive derivative is an ester, the temperature is preferably from 50° to 100° C. The reaction time is usually from 0.1 to 24 hours.

A compound of the formula (I) wherein m is 1, i.e. a compound of the following formula (I-2), can be produced by reacting a compound of the above formula (I-1) with an oxidizing agent.

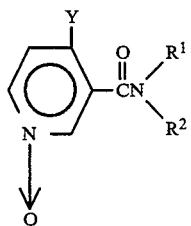

(I-2)

wherein Y, $R^1$ and $R^2$ are as defined above.

This reaction is conducted usually in the presence of a solvent. As the solvent, acetic acid may, for example, be mentioned. As the oxidizing agent, hydrogen peroxide is usually employed. The reaction temperature is usually from 50° to 100° C., and the reaction time is usually from 6 to 24 hours.

A compound of the formula (I) wherein X is a sulfur atom, can be produced by reacting a compound of the above formula (I-1) with a sulfurization agent such as phosphorus pentasulfide.

This reaction is conducted usually in the presence of a solvent. As the solvent, an aromatic hydrocarbon such as toluene or xylene is preferably used. The reaction temperature for the above reaction is usually from 80° to 150° C., preferably from 110° to 130° C. The reaction time is usually from 1 to 12 hours.

Further, the compound of the formula (I) or its salt may be prepared, for example, by the following method (B):

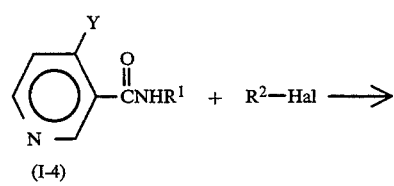

(B)

(I-4)

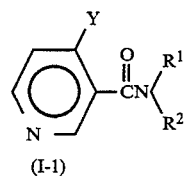

(I-1)

In the above formulas, Y, $R^1$ and $R^2$ are as defined above, provided that here, $R^2$ is other than a hydrogen atom, and Hal is a halogen atom.

The reaction of the method (B) can be conducted in the same manner as the reaction of the above method (A).

Further, the following methods may, for example, be mentioned as other methods for producing the compounds of the formula (I) or their salts:

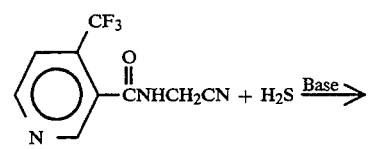

(C-1)

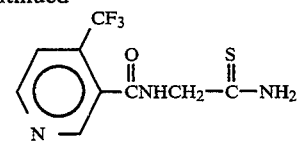

-continued

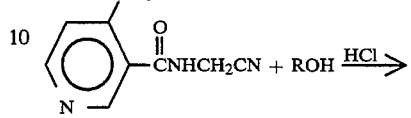

(C-2)

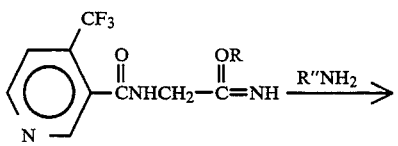

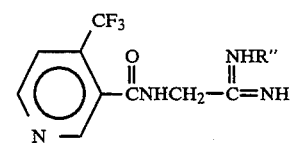

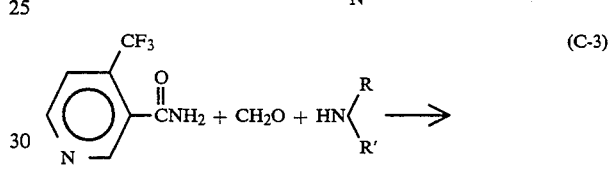

(C-3)

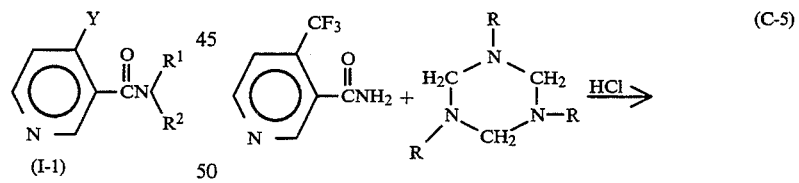

(C-4)

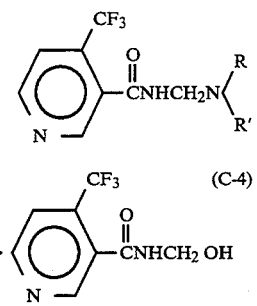

(C-5)

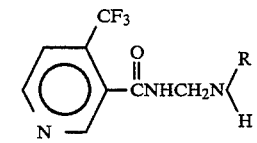

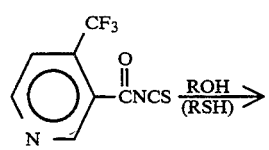

(C-6)

-continued

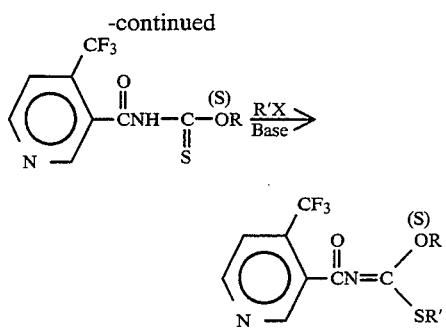

In the above formulas, R and R' are alkyl groups and R" is a hydrogen atom or an alkyl group.

The reaction of the above method (C-1) can be conducted in the presence of a solvent and a base. The solvent may, for example, be an aromatic hydrocarbon such as benzene or toluene; an ether such as diethyl ether or tetrahydrofuran; a halogenated hydrocarbon such as methylene chloride or chloroform; or an aprotic polar solvent such as acetonitrile, dimethylformamide or pyridine. These solvents may be used alone or in combination as a mixture. As the base, a tertiary base such as triethylamine or pyridine is preferred. The reaction temperature of the above reaction is usually from 0° to 50° C., preferably from 20° to 40° C., and the reaction time is usually from 1 to 6 hours.

The reaction of the first half of the above method (C-2) can be conducted in the presence of hydrogen chloride gas and a solvent. The solvent may, for example, be an ether such as tetrahydrofuran or diethyl ether; a halogenated hydrocarbon such as methylene chloride or chloroform; or an aromatic hydrocarbon such as benzene or nitrobenzene. These solvents may be used alone or in combination as a mixture. The reaction temperature is usually from −10+ to +30° C., preferably from −5° to +10° C., and the reaction time is usually from 4 to 168 hours.

The reaction of the latter half can be conducted in the presence of a solvent. The solvent may, for example, be an alcohol such as methanol or ethanol. The reaction temperature is usually from 0° to 80° C., preferably from 20° to 50° C., and the reaction time is usually from 1 to 8 hours.

The reaction of the above method (C-3) can be conducted in the presence of a solvent. The solvent may, for example, be water or an alcohol such as methanol or ethanol. Such solvents may be used alone or in combination as a mixture. The reaction temperature is usually from 10° to 100° C., preferably from 20° to 80° C., and the reaction time is usually from 1 to 12 hours.

The reaction of the above method (C-4) can be conducted under the same conditions as in the method (C-3).

The reaction of the above method (C-5) can be conducted in the presence of hydrogen chloride gas and a solvent. The solvent may, for example, be an ether such as dimethoxyethane or dioxane. The reaction temperature is usually from −50° to +50° C., preferably from −30° to 20° C. The reaction time is usually from 1 to 8 hours.

The reactions of the above method (C-6) are three-step reactions. The reaction in the first step is conducted in the presence of a solvent. The solvent may, for example, be an aromatic hydrocarbon such as benzene or toluene; an ether such as diethyl ether or tetrahydrofuran; a halogenated hydrocarbon such as methylene chloride or chloroform; or an aprotic polar solvent such as acetonitrile or dimethylformamide. Such solvents may be used alone or in combination as a mixture. The reaction temperature is usually from 30° to 120° C., preferably from 50° to 80° C., and the reaction time is usually from 1 to 12 hours.

The reaction in the second step is conducted in the presence of a solvent. The solvent may, for example, be the same solvent as mentioned for the reaction of the above first step. The reaction temperature is usually from 0° to 100° C., preferably from 20° to 50° C., and the reaction time is usually from 1 to 12 hours.

The reaction in the third step is conducted in the presence of a solvent and a base. The solvent may, for example, be an aprotic polar solvent such as acetonitrile or dimethylformamide. The base may, for example, be an alkali metal hydride such as sodium hydride or potassium hydride; an alkali metal hydroxide such as sodium hydroxide or potassium hydroxide; an alkali metal alkoxide such as sodium methoxide or sodium ethoxide; or a tertiary amine such as triethylamine or pyridine. The reaction temperature is usually from 0° to 100° C., preferably from 20° to 50° C., and the reaction time is usually from 1 to 12 hours.

Among the compounds of the formula (I), a compound wherein X is an oxygen atom, Y is $CF_3$, and $R^1$ and $R^2$ are simultaneously hydrogen atoms, i.e. 4-trifluoromethyl-3-pyridine carboxamide, can be prepared by the above method (A) using ammonia as the compound of the formula (III). Otherwise, it can be prepared by the following method from 2,6-dichloro-3-cyano-4-trifluoromethylpyridine:

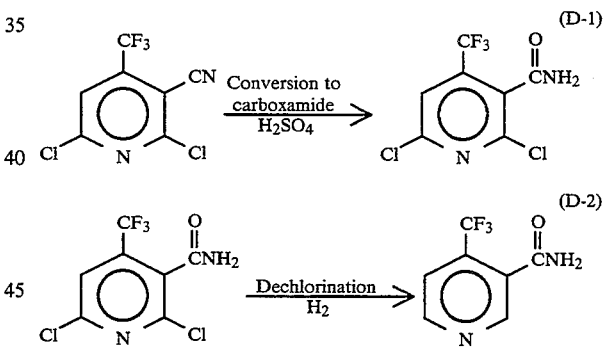

Step (D-1) is conducted by reacting 2,6-dichloro-3-cyano-4-trifluoromethylpyridine with concentrated sulfuric acid.

Step (D-2) is conducted by reacting hydrogen and 2,6-dichloro-4-trifluoromethyl-3-pyridine carboxamide obtained in the above step (D-1), in the presence of a solvent, a catalyst and a base. The solvent may, for example, be an alcohol such as methanol or ethanol, or an ether such as tetrahydrofuran. The catalyst may, for example, be palladium or palladium (II) chloride. The base may, for example, be sodium acetate, sodium hydroxide, potassium hydroxide or triethylamine.

The temperature for the reaction of step (D-2) is usually from 0° to 100° C., and the reaction time is usually from 1 to 24 hours.

Further, in the above step (D-1), a similar reaction can be conducted by using 2,6-dibromo-3-cyano-4-trifluoromethylpyridine instead of 2,6-dichloro-3-cyano-4-trifluoromethylpyridine. This 2,6-dibromo-3-cyano-4-trifluoromethylpyridine can be obtained by reacting 3-cyano-2,6-dihydroxy-4-trifluoromethylpyridine with a brominating agent such as phosphorus oxybromide.

Among these compounds of the formula (II), a compound wherein Y is $CF_3$, i.e. 4-trifluoromethylpyridine-3-carboxylic acid is a known compound and is commercially available.

Further, 4-haloalkylpyridine-3-carboxylic acid can be produced, for example, by the following method.

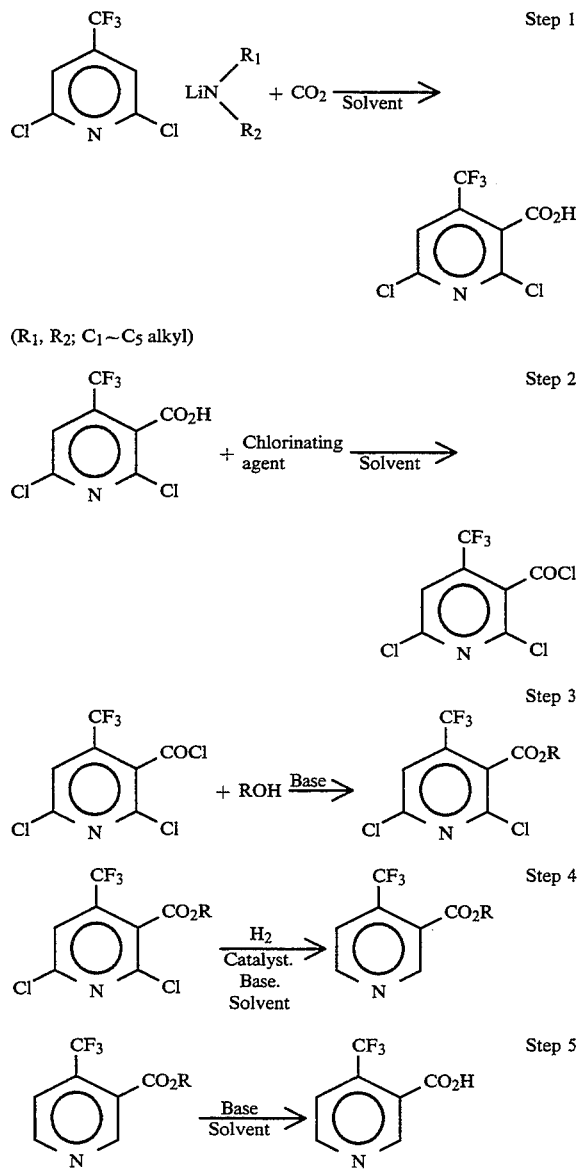

($R_1$, $R_2$; $C_1 \sim C_5$ alkyl)

Step 1

The Step 1 can be conducted by reacting 2,6-dichloro4-haloalkylpyridine with gaseous or solid carbon dioxide in the presence of lithium dialkylamide (preferably lithium diisopropylamide) and a solvent. The solvent may be an ether such as tetrahydrofuran or diethyl ether. A reaction temperature is usually from $-100°$ to $+20°$ C., preferably from $-80°$ to $-20°$ C. and a reaction time is from 1 to 12 hours.

Step 2

The Step 2 can be conducted by reacting 2,6-dichloro4-haloalkylpyridine-3-carboxylic acid formed in the Step 1 with a chlorinating agent in the presence of a solvent. The chlorinating agent may be thionyl chloride or phosphorus pentachloride, and the solvent may be an aromatic hydrocarbon such as benzene or toluene. A reaction temperature is usually from 20° to 120° C., preferably from 50° to 100° C., and a reaction time is from 1 to 6 hours.

Step 3

The Step 3 can be conducted by reacting chloride of 2,6-dichloro-4-haloalkylpyridine-3-carboxylic acid formed in the Step 2 with alcohol in the presence of a base. The alcohol may be an alcohol such as methanol or ethanol, and the base may be a tertiary base such as triethylamine or pyridine. A reaction temperature is usually from 0° to 80° C., preferably from 20° to 50° C., and a reaction time is from 1 to 12 hours.

Step 4

The Step 4 can be conducted by reacting ester of 2,6-dichloro-4-haloalkylpyridine-3-carboxylic acid formed in the Step 3 with hydrogen gas in the presence of a solvent, catalyst and base. The solvent may be an alcohol such as methanol or ethanol or an ether such as tetrahydrofuran, the catalyst may be a palladium or palladium chloride (II), and the base may be a tertiary base such as triethylamine or pyridine, or sodium acetate. A reaction temperature is usually from 0° to 100° C., preferably from 20° to 50° C., and a reaction time is from 1 to 24 hours.

Step 5

The Step 5 can be conducted by reacting ester of 4-haloalkylpyridine-3-carboxylic acid formed in the Step 4 with a base in the presence of a solvent. The solvent may be water or an alcohol such as methanol or ethanol and used alone or in combination as a mixture. The base may be an alkali metallic hydroxide such as sodium hydroxide or potassium hydroxide. A reaction temperature is usually from 0° to 100° C., preferably from 20° to 80° C., and a reaction time is from 1 to 12 hours.

Furthermore, its reactive derivative can be produced from the compound of the formula (II).

The synthesis of an acid chloride can be conducted by reacting 4-haloalkylpyridine-3-carboxylic acid with a chlorinating agent such as thionyl chloride or phosphorus trichloride, if necessary, in the presence of a catalytic amount of dimethylformamide at a refluxing temperature.

A reactive derivative of the formula (II) other than 4-haloalkyl-3-pyridine carbonyl chloride can be produced by a method similar to the conventional method for converting benzoic acid to the reactive derivative. For example, an acid bromide can be produced by reacting 4-haloalkylpyridine-3-carboxylic acid with a brominating agent such as phosphorus tribromide, phosphorus oxybromide or acetyl bromide; an acid anhydride can be produced by reacting 4-haloalkylpyridine-3-carboxylic acid or its chloride with a drying agent; and an ester can be produced by reacting 4-haloalkylpyridine-3carboxylic acid with an alcohol.

The compounds of the present invention show excellent activities as active ingredients for pesticides, for example, insecticides, miticides, nematicides and soil pesticides. For instance, they are effective against plant parasitic mites such as two-spotted spider mite (*Tetrany-* chus urticae), carmine spider mite (*Tetranychus cinnabarinus*) or citrus red mite (*Panonychus citri*) or bulb mite (*Rhizoglyphus echinopus*); aphids such as green peach aphid (*Myzus persicae*) or cotton aphid (*Aphis gossypii*); agricultural insect pests such as diamondback moth (*Plutella xylostella*), cabbage armyworm (*Mamestra brassicae*), common cutworm (*Spodoptera litura*), colorado potato beetle (*Leptinotarsa decemlineata*), codling moth (*Laspeyresia pomonella*), bollworm (*Heliothis zea*), tobacco budworm (*Heliothis virescens*), boll weevil (*Anthonomus grandis*), gypsy moth (*Lymantria dispar*), cucurbit leaf beetle (*Aulacophora femoralis*), planthoppers, leafhoppers, scales, bugs, whiteflies, thrips, grasshoppers, anthomyiid flies, scarabs, black cutworm (*Agrotis ipsilon*), cutworm (*Agrotis segetum*) or ants; hygienic insect pests such as tropical rat mite (*Ornithonyssus bacoti*), cockroaches, housefly (*Musca domestica*) or house mosquito (*Culex pipiens pallens*); stored grain insect pests such as angoumois grain moth (*Sitotroga cerealella*), azuki bean weevil (*Callosobruchus chinensis*), confused flour beetle (*Tribolium confusum*) or mealworms; household goods insect pests such as casemaking clothes moth (*Tinea pellionella*), black carpet beetle (*Anthrenus scrophularidae*) or subterranean termites; and other parasites on domestic animals such as fleas, lice or flies. Further, they are also effective against plant parasitic nematodes such as root-knot nematodes, cyst nematodes, root-lesion nematodes, rice white-tip nematode (*Aphelenchoides besseyi*), strawberry bud nematode (*Nothotylenchus acris*) or pine wood nematode (*Bursaphelenchus lignicolus*). Furthermore, they are effective also against the soil pests. Here, the soil pests include gastropods such as slugs or snails, or isopods such as pillbugs or sowbugs. Among them, the compounds of the present invention are particularly effective against aphids such as green peach aphid or cotton aphid. Further, they are effective against insect pests such as aphids having acquired resistance to organophosphorus, carbamate and/or synthetic pyrethroid insecticides. Moreover, the compounds of the present invention have excellent systemic properties, and by the application of the compounds of the present invention to soil treatment, not only noxious insects, noxious mites, noxious nematodes, noxious gastropods and noxious isopods in soil but also foliage pests can be controlled.

When used as active ingredients for insecticides, miticides, nematicides or soil pesticides, the compounds of the present invention may be formulated together with agricultural adjuvants into various forms such as dusts, granules, water dispersible granules, wettable powders, emulsifiable concentrates, suspension concentrates, soluble concentrates, water soluble powders, flowables, aerosols or pastes, ultra low-volume formulations, and just like conventional agricultural chemicals. When such formulations are to be actually used, they may be used as they are or after being diluted with suitable diluents such as water to a predetermined concentration.

Such formulations are usually composed of 0.1–90 parts by weight of active ingredient and 10–99.9 parts by weight of agricultural adjuvants.

As the agricultural adjuvants, there may be mentioned carriers, emulsifiers, suspending agents, dispersants, extenders, penetrating agents, wetting agents, thickeners or stabilizers. They may be added as the case requires. The carriers may be classified into solid carriers and liquid carriers. As the solid carriers, there may be mentioned powders of animal and plant origin, such as starch, activated carbon, soybean flour, wheat flour, wood powder, fish powder or powdered milk; or mineral powders such as talc, kaolin, bentonite, calcium carbonate, zeolite, diatomaceous earth, white carbon, clay or alumina. As the liquid carriers, there may be mentioned water; alcohols such as isopropyl alcohol or ethylene glycol; ketones such as cyclohexanone or methyl ethyl ketone; ethers such as dioxane or tetrahydrofuran; aliphatic hydrocarbons such as kerosine gas oil or the like; aromatic hydrocarbons such as xylene, trimethylbenzene, tetramethylbenzene, methylnaphthalene or solvent naphtha; halogenated hydrocarbons such as chlorobenzene; acid amides such as dimethylacetamide; esters such as glycerine ester of a fatty acid; nitriles such as acetonitrile; or sulfur-containing compounds such as dimethyl sulfoxide.

Further, the compounds of the present invention may be used in combination with other agricultural chemicals such as insecticides, miticides, nematicides, fungicides, antiviral agents, attractants, herbicides or plant growth regulators, as the case requires. In some cases, the effectiveness will be improved by such combination.

For instance, as such insecticides, miticides or nematicides, there may be mentioned as follows.

Organic Phosphate Compounds

O-(4-bromo-2-chlorophenyl) O-ethyl S-propyl phosphorothioate (common name: Profenofos),
O-(2,2-dichlorovinyl) O,O-dimethylphosphate (common name: Dichlorovos),
O-ethyl O-[3-methyl-4-(methylthio)phenyl] N-isopropyl phosphoramidate (common name: Fenamiphos),
O,O-dimethyl O-(4-nitro-m-tolyl) phosphorothioate (common name: Fenitrothion),
O-ethyl O-(4-nitrophenyl)phenyl phosphonothioate (common name: EPN),
O,O-diethyl O-(2-isopropyl-6-methylpyrimidin-4-yl) phosphorothioate (common name: Diazinon),
O,O-dimethyl O-(3,5,6-trichloro-2-pyridyl) phosphorothioate (common name: Chlorpyrifos-methyl),
O,S-dimethyl N-acetylphosphoramidothioate (common name: Acephate),
O-(2,4-dichlorophenyl) O-ethyl S-propyl phosphorodithioate (common name: Prothiofos), and
(RS)-S-sec-butyl O-ethyl 2-oxo-1,3-thiazolidin-3-yl phosphonothioate (common name: Fosthiazate);

Carbamate Compounds 1-naphthyl N-methylcarbamate (common name: Carbaryl),
2-isopropoxyphenyl N-methylcarbamate (common name: Propoxur),
2-methyl-2-(methylthio)propionaldehyde O-methylcarbamoyloxime (common name: Aldicarb), (common name: Aldicarb),
2,3-dihydro-2,2-dimethylbenzofuran-7-yl N-methylcarbamate (common name: Carbofuran),
dimethyl N,N'-[thiobis[(methylimino)carbonyloxy]] bisethanimidothioate (common name: Thiodicarb),
S-methyl N-(methylcarbamoyloxy)thioacetimidate (common name: Methomyl),
N,N-dimethyl-2-methylcarbamoyloxyimino-2-(methylthio) acetamide (common name: Oxamyl),
2-(ethylthiomethyl)phenyl N-methylcarbamate (common name: Ethiofencarb),
2-dimethylamino-5,6-dimethylpyrimidin-4-yl N,N-dimethylcarbamate (common name: Pirimicarb), and 2-sec-butylphenyl N-methylcarbamate (common name: Fenobucarb);

Nereistoxin Derivatives

S,S'-2-dimethylaminotrimethylenebis(thiocarbamate) (common name: Cartap), and
N,N-dimethyl-1,2,3-trithian-5-ylamine (common name: Thiocyclam);

Organic Chlorine Compounds 2,2,2-trichloro-1,1-bis(4-chlorophenyl)ethanol (common name: Dicofol), and
4-chlorophenyl-2,4,5-trichlorophenylsulfone (common name: Tetradifon);

Organometallic Compounds bis[tris(2-methyl-2-phenylpropyl)tin] oxide (common name: Fenbutatin Oxide);

Pyrethroid Compounds (RS)-α-cyano-3-phenoxybenzyl (RS)-2-(4-chlorophenyl)-3-methylbutylate (common name: Fenvalerate),
3-phenoxybenzyl (1RS)-cis,trans-3-(2,2-dichlorovinyl)-2,2-dimethylcyclopropanecarboxylate (common name: Permethrin),
(RS)-α-cyano-3-phenoxybenzyl (1RS)-cis,trans-3-(2,2-dichlorovinyl)-2,2-dimethylcyclopropanecarboxylate (common name: Cypermethrin),
(S)-α-cyano-3-phenoxybenzyl (1R)-cis-3-(2,2-dibromovinyl)-2,2-dimethylcyclopropanecarboxylate (common name: Deltamethrin),
(RS)-α-cyano-3-phenoxybenzyl (1RS)-cis,trans-3-(2-chloro-3,3,3-trifluropropenyl)-2,2-dimethylcyclopropanecarboxylate (common name: Cyhalothrin), p0 4-methyl-2,3,5,6-tetrafluorobenzyl-3-(2-chloro-3,3,3-trifluoro-1-propenyl)-2,2-dimethylcyclopropanecarboxylate (common name: Tefluthrin), and
2-(4-ethoxyphenyl)-2-methylpropyl 3-phenoybenzyl ether (common name: Ethofenprox);

Benzoylurea Compounds 1-(4-chlorophenyl)-3-(2,6-difluorobenzoyl)urea (common name: Diflubenzuron),
1-[3,5-dichloro-4-(3-chloro-5-trifluoromethyl-2-pyridyloxy)phenyl]-3-(2,6-difluorobenzoyl)urea (common name: Chlorofluazuron), and
1-(3,5-dichloro-2,4-difluorophenyl)-3-(2,6-difluorobenzoyl)urea (common name: Teflubenzuron);

Juvenile Hormone-like Compounds isopropyl (2E,4E)-11-methoxy-3,7,11-trimethyl-2,4-dodecadienoate (common name: Methoprene);

Pyridazinone Compounds 2-t-butyl-5-(4-t-butylbenzylthio)-4-chloro-3(2H) pyridazinone (common name: Pyridaben);

Pyrazole Compounds t-butyl 4-[(1,3-dimethyl-5-phenoxypyrazol-4-yl)methyleneamino-oxymethyl]benzoate (common name: Fenpyroximate);
5-amino-1-(2,6-dichloro-α,α,α-trifluoro-p-tolyl)-4-trifluoromethylsulphinylpyrazole-3-carbonitrile (common name: fipronil);
N-(4-tert-butylbenzyl)-4-chloro-3-ethyl-1-methylpyrazole-5-carboxamide (common name: tebufenpyrad);

Nitro Compounds 1-(6-chloro-3-pyridylmethyl)-N-nitro-imidazolidin-2-ylideneamine (common name: Imidacloprid),
1-[N-(6-chloro-3-pyridylmethyl)-N-ethylamino]-1-methylamino-2-nitroethylene (common name: nitenpyram), $N^1$-[(6-chloro-3-pyridyl)methyl]-$N^2$-cyano-$N^1$-methyl acetamidine (European Patent Laid-Open No. 456826),
1-(6chloro-3-pyridylmethyl)-2-(1-nitro-2-allylthioethylidene)imidazolidine (European Patent Laid-Open No. 437,784),
1-(6-chloro-3-pyridylmethyl)-2-(1-nitro-2-ethylthioethylidene)imidazolidine (European Patent Laid-Open No. 437,784), and
1-(6-chloro-3-pyridylmethyl)-2-(1-nitro-2-β-methylallylthioethylidene)imidazolidine (European Patent Laid-Open No. 437,784);

Hydrazine Compounds

N'-t-butyl-N'-3,5-dimethylbenzoyl-N-benzo[b]-thiophene-2-carbohydrazide,
N'-t-butyl-N'-3,5-dimethylbenzoyl-N-4,5,6,7-tetrahydrobenzo[b]thiophene-2-carbohydrazide,
N'-t-butyl-N'-3,5-dimethylbenzoyl-N-5,6-dihydro-4H-cyclopenta[b]thiophene-2-carbohydrazide and
N'-t-butyl-N'-3',5'-dimethylbenzoyl-N-4-ethylphenylcarbohydrazide (common name: tebufenozide).

Dinitro Compounds
Organic Sulfur Compounds
Urea Compounds
Triazine Compounds
Hydrazone Compounds

Other Compounds 2-tert-butylamino-3-isopropyl-5-phenyl-3,4,5,6-tetrahydro-2H-1,3,5-thiadiazin-4-one (common name: Buprofezin),
trans-(4-chlorophenyl)-N-cyclohexyl-4-methyl-2-oxothiazolidinone-3-carboxamide (common name: Hexythiazox),
N-methylbis(2,4-xylyliminomethyl)amine (common name: Amitraz),
N'-(4-chloro-o-tolyl)-N,N-dimethylformamidine (common name: Chlorodimeform), and
(4-ethoxyphenyl)-[3-(4-fluoro-3-phenoxyphenyl)-propyl](dimethyl)silane (common name: Silafluofen).
ethyl (3-tert-butyl-1-dimethylcarbamoyl-1H-1,2,4-triazol-5-ylthio)acetate (common name: triazamate)
4,5-dihydro-6-methyl-4-(3-pyridylmethyleneamino)-1,2,4-triazin-3(2H)-one (common name: pymetrozine)
5-chloro-N-{2-[4-(2-ethoxyethyl)-2,3-dimethylphenoxy]ethyl}-6-ethylpyrimidin-4-amine (common name: pyrimidifen)
4-bromo-2-(4-chlorophenyl)-1-ethoxymethyl-5-trifluoromethyl pyrrole-3-carbonitrile (Japanese Unexamined Patent Publication No. 104042/1989)

The compound of the present invention may also be used in admixture or combination with microbial agricultural chemicals such as B. T. and insect viruses, and antibiotics such as avermectin and milbemycin.

Specific Examples of active ingredients of the aforementioned fungicides include the following compounds:

Pyrimidinamine Compounds 2-anilino-4-methyl-6-(1-propynyl)pyrimidine(disclosed in Japanese Unexamined Patent Publication No. 208,581/1988).

Azole Compounds 1-(4-chlorophenoxy)-3,3-dimethyl-1-(1H-1,2,4-triazol-1-yl)butanone (common name: Triadimefon), 1-(biphenyl-4-yloxy)-3,3-dimethyl-1-(1H-1,2,4-triazol-1-yl)butan-2-ol (common name: Bitertanol), 1-[N-(4-chloro-2-trifluoromethylphenyl)-2-propoxyacetimidoyl]imidazole (common name: Triflumizole), 1-[2-(2,4-dichlorophenyl)-4-ethyl-1,3-dioxolan-2-ylmethyl]-1H-1,2,4-triazole (common name: Etaconazole)

1-[2-(2,4-dichlorophenyl)-4-propyl-1,3-dioxolan-2-ylmethyl]-1H-1,2,4-triazole (common name: propiconazole)

1-[2-(2,4-dichlorophenyl)pentyl]-1H-1,2,4-triazole (common name: Penconazole)

bis(4-fluorophenyl)(methyl)(1H-1,2,4-triazole-1-ylmethyl)silane (common name: Flusilazole), 2-(4-chlorophenyl)-2-(1H-1,2,4-triazole-1-yl-methyl)-hexanenitrile (common name: Myclobutanil), (2RS,3RS)-2-(4-chlorophenyl)-3-cyclopropyl-1-(1H-1,2,4-triazole-1-yl)butan-2-ol (common name: Cyproconzole), (RS)-1-(4-chlorophenyl)-4,4-dimethyl-3-(1H-1,2,4-triazol-1-ylmethyl)pentan-3-ol (common name: Terbuconazole), (RS)-2-(2,4-dichlorophenyl)-1-(1H-1,2,4-triazole-1-yl)hexan-2-ol (common name: Hexaconazole), (2RS,5RS)-5-(2,4-dichlorophenyl)tetrahydro-5-(1H-1,2,4-triazole-1-ylmethyl)-2-furyl 2,2,2-trifluoroethyl ether (common name: Furconazole-cis), and N-propyl-N-[2-(2,4,6-trichlorophenoxy)ethyl]imidazole-1-carboxamide (common name: Prochloraz);

Quinoxaline Compounds 6-methyl-1,3-dithiolo[4,5-b]quinoxalin-2-one (common name: Quinomethionate);

Dithiocarbamate Compounds manganese ethylenebis(dithiocarbamate) polymer (common name: Maneb), zinc ethylenebis(dithiocarbamate) polymer (common name: Zineb), complex of zinc with manganese ethylenebis-(dithiocarbamate) (Maneb) (common name: Mancozeb), dizinc bis(dimethyldithiocarbamate) ethylenebis-(dithiocarbamate) (common name: Polycarbamate), and zinc propylenebis(dithiocarbamate) polymer (common name: Propineb);

Organic Chlorine Compounds 4,5,6,7-tetrachlorophathalide (common name: Fthalide), tetrachloroisophthalonitrile (common name: Chlorothalonil), and pentachloronitrobenzene (common name: Quintozene);

Benzimidazole Compounds methyl 1-(butylcarbamoyl)benzimidazol-2-yl-carbamate (common name: Benomyl), dimethyl 4,4'-(o-phenylene)bis(3-thioallophanate) (common name: Thiophanate-Methyl), and methyl benzimidazole-2-ylcarbamate (common name: Carbendazim);

Pyridinamine Compounds 3-chloro-N-(3-chloro-2,6-dinitro-4-α,α,α-trifluorotolyl)-5-trifluoromethyl-2-pyridinamine (common name: Fluazinam);

Cyanoacetamide Compounds 1-(2-cyano-2-methoxyiminoacetyl)-3-ethylurea (common name: Cymoxanil);

Phenylamide compounds methyl N-(2-methoxyacetyl)-N-(2,6-xylyl)-DL-alaninate (common name: Metalaxyl), 2-methoxy-N-(2-oxo-1,3-oxazolidin-3-yl)aceto-2',6'-xylidide (common name: Oxadixyl), (±)-α-2-chloro-N-(2,6-xylylacetamido)-γ-butyrolactone (common name: Ofurace), methyl N-phenylacetyl-N-(2,6-xylyl)-DL-alaninate (common name: Benalaxyl), methyl N-(2-furoyl)-N-(2,6-xylyl)-DL-alaninate (common name: Furalaxyl), and (±)-α-[N-(3-chlorophenyl)cyclopropanecarboxamido]-γ-butyrolactone (common name: Cyprofuram);

Sulfenic Acid Compounds

N-dichlorofluoromethylthio-N',N'-dimethyl-N-phenylsulfamide (common name: Dichlofluanid);

Copper Compounds cupric hydroxide (common name: cupric hydroxide), and copper 8-quinolinolate (common name: Oxine-Copper);

Isoxazole Compounds 5-methylisoxazol-3-ol (common name: Hydroxyisoxazole);

Organophosphorus Compounds aluminum tris(ethyl phosphonate) (common name: Fosetyl-Al), O-2,6-dichloro-p-tolyl-O,O-dimethyl phosphorothioate (common name: Tolcofos-methyl), S-benzyl O,O-diisopropyl phosphorothioate, O-ethyl S,S-diphenyl phosphorodithioate, and aluminum ethyl hydrogenphosphonate;

N-Halogenothioalkyl Compounds

N-(trichloromethylthio)cyclohex-4-ene-1,2-di-carboximide (common name: Captan),

N-(1,1,2,2-tetrachloroethylthio)cyclohex-4-ene-1,2-dicarboximide (common name: Captafol), and N-(trichloromethylthio)phthalimide (common name: Folpet);

Dicarboximide Compounds

N-(3,5-dichlorophenyl)-1,2-dimethylcyclopropane-1,2-dicarboximide (common name: Procymidone), 3-(3,5-dichlorophenyl)-N-isopropyl-2,4-dioxoimidazolidine-1-carboxamide (common name: Iprodione), and (RS)-3-(3,5-dichlorophenyl)-5-methyl-5-vinyl-1,3-oxazolidine-2,4-dione (common name: Vinclozolin);

Benzanilide Compounds

α,α,α-trifluoro-3'-isopropoxy-o-toluanilide (common name: Flutolanil), and
3'-isopropoxy-o-toluanilide (common name: Mepronil);

Benzamide Compounds 2-(1,3-dimethylpyrazol-4-ylcarbonylamino)-4-methyl-3-penetenenitrile (disclosed in British Patent No. 2,190,375), and
α-(nicrotinyulamino)-(3-fluorophenyl)acetonitrile (disclosed in Japanese Patent Laid Open No. 135,364/1998);

Piperazine Compounds

N,N'-[piperazine-1,4-diylbis[trichloromethyl)methylene]]diformamide (common name: Triforine);

Pryidine Compounds

2'4'-dichloro-2-(3-pyridyl)acetophenone O-methyloxime (common name: Pyrifenox);

Carbinol Compounds (±)-2,4'-dichloro-α-(pyrimidin-5-yl)benzhydryl alcohol (common name: Fenarimol), and
(±)-2,4'-difluoro-α-(1H-1,2,4-triazol-1-yl-methyl)benzhydryl alcohol (common name: Flutriafol);

Piperidine Compounds (RS)-1-[3-(4-tert-butylphenyl)-2-methylpropyl]piperidine (common name: Fenpropidine);

Morpholine Compounds (±)-cis-4-[3-(4-tert-butylphenyl)-2-methylpropyl]-2,6-dimethylmorpholine (common name: Fenpropimorph);

Organotin Compounds triphenyltin hydroxide (common name: Fentin Hydroxide), and
triphenyltin acetate (common name: Fentin Acetate);

Urea Compounds 1-(4-chlorobenzyl)-1-cyclopentyl-3-phenylurea (common name: Pencycuron);

Cinnamic Acid Compounds (E,Z)4-[3-(4-chlorophenyl)-3-(3,4-dimethoxyphenyl)acryloyl]morpholine (common name: Dimethomorph);

Phenylcarbamate Compounds isopropyl 3,4-diethoxycarbanilate (common name: Diethofencarb);

Cyanopyrrol Compounds 3-cyano-4-(2,2-difluoro-1,3-benzodioxol-4-yl)pyrrole (trade name: Saphire), and
3-(2',3'-dichlorophenyl)-4-cyanopyrrole (common name: Fenpiclonil).

Pyridinamine Compounds 3-chloro-N-(3-chloro-2,6-dinitro-4-α,α,α-trifluorotolyl)-5-trifluoromethyl-2-pyridinamine (common name: fluazinam).

Other active ingredients of the fungicides include anthraquinone compounds, crotonic acid compounds, antibiotics and other compounds such as diisopropyl 1,3-dithiolan-2-ylidenemalonate (common name: isoprothiolane), 5-methyl-1,2,4-triazolo[3,4-b]benzothiazole (common name: tricyclazole), 1,2,5,6-tetrahydropyrrolo[3,2,1-ij]-quinoline-4-one (common name: pyroquilon), 6-(3,5-dichloro-4-methylphenyl)-3(2H)-pyridazinone (common name: diclomezine, 3-allyloxy-1,2-benzisothiazole-1,1-dioxide (common name: probenazole).

The suitable blending weight ratio of the compound of the present invention to the other agricultural chemical(s) when used in admixture or combination may generally be in the range of 1:300 to 300:1, and preferably in the range in 1:100 to 100:1.

The pesticides of the present invention are applied in an active ingredient concentration of from 0.1 to 500,000 ppm, preferably from 1 to 100,000 ppm. The active ingredient concentration may optionally be changed depending upon the formulation, the manner, purpose, timing or place of the application and the condition of the insect pests. For instance, aquatic noxious insects can be controlled by applying the formulation having the above-mentioned concentration to the site of the outbreak, and thus, the concentration of the active ingredient in water is less than the above-mentioned range.

The amount of the application of the active ingredient per unit surface area is usually from about 0.1 to 5,000 g, preferably from 10 to 1,000 g, per hectare. However, in a certain special case, the amount of the application may be outside the above range.

Various formulations containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a food containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

Further, the application of the pesticides of the present invention includes, in addition to their direct application to pests, any other application wherein the amide compounds of the formula (I) or their salts act on the pests. As such other-application, a case may be mentioned in which other effective compounds are decomposed to amide compounds of the formula (I) in the environment such as in the soil, which will then act on the pests.

Now, the present invention will be described with reference to Examples. However, it should be understood that the present invention is by no means restricted by these specific Examples.

SYNTHESIS EXAMPLE 1

Preparation of N-cyanomethyl-4-trifluoromethyl-3-pyridine carboxamide (Compound No. 1)

A solution of 0.96 g of 4-trifluoromethyl-3-pyridine carboxylic acid and 1.19 g of thionyl chloride in 5 ml of benzene was refluxed under heating for 30 minutes in the presence of a catalytic amount of dimethylformamide. Excess thionyl chloride and benzene were distilled off under reduced pressure. Then, the residue was dissolved in 15 ml of tetrahydrofuran. Then, 1.82 g of triethylamine and 1.05 g of aminoacetonitrile sulfate were added thereto, and the mixture was stirred at room temperature for 18 hours. Then, the mixture was poured into water and extracted with ethyl acetate. The organic layer was washed with an aqueous ammonium chloride solution, water and a saturated sodium chloride aqueous solution, dried over anhydrous sodium sulfate and then concentrated under reduced pressure. The residue was purified by silica gel column chromatography to obtain 0.50 g of the desired product (Compound No. 1) having a melting point of from 155° to 161° C.

SYNTHESIS EXAMPLE 2

Preparation of N-allyl-4-trifluoromethyl-3-pyridine carboxamide (Compound No. 22)

A solution of 0.26 g of 4-trifluoromethyl-3-pyridine carboxylic acid and 0.24 g of thionyl chloride in 10 ml of benzene was refluxed under heating for 30 minutes in the presence of a catalytic amount of dimethylformamide. Excess thionyl chloride and benzene were distilled off under reduced pressure. Then, the residue was dissolved in 15 ml of tetrahydrofuran. Then, 0.21 g of triethylamine and 0.12 g of allylamine were added thereto, and the mixture was stirred at room temperature for 20 hours. Then, the mixture was poured into an aqueous ammonium chloride solution and extracted with ethyl acetate. The organic layer was washed with water and a saturated sodium chloride aqueous solution, dried over anhydrous sodium sulfate and then concentrated under reduced pressure. The residue was purified by silica gel column chromatography to obtain 0.21 g of the desired product (Compound No. 22) having a melting point of from 75.5° to 77° C.

SYNTHESIS EXAMPLE 3

Preparation of 4-trifluoromethyl-3-pyridine carboxamide (Compound No. 5)

A solution comprising 3 g of 4-trifluoromethyl-3-pyridine carboxylic acid, 6.7 ml of thionyl chloride and 20 ml of benzene, was refluxed under heating for 1.5 hours in the presence of a catalytic amount of dimethylformamide. Excess thionyl chloride and benzene were distilled off. Then, the residue was dissolved in 5 ml of ethyl acetate. This solution was gradually dropwise added to 20 ml of ammonia under cooling with ice. After completion Of the dropwise addition, the mixture was stirred at room temperature for 30 minutes. Then, water and ethyl acetate were distilled off under reduced pressure. The residue was extracted with heated ethyl acetate to obtain 2.1 g of 4-trifluoromethyl-3-pyridine carboxamide (melting point: 162.7° C.) as the desired product.

SYNTHESIS EXAMPLE 4

Preparation of 4-trifluoromethyl-3-pyridine carboxamide (Compound No. 5)

(1) 11.3 g of 3-cyano-2,6-dichloro-4-trifluoromethylpyridine was gradually added to 22.6 ml of concentrated sulfuric acid, and then the mixture was heated and reacted at 100° C. for one hour. After completion of the reaction, the mixture was poured into ice water, whereupon white precipitates formed. The precipitates were collected by filtration, and the filtrate was extracted with methylene chloride. The organic layer was dried over anhydrous sodium sulfate, and then the solvent was distilled off under reduced pressure to obtain a white solid. This solid and the precipitates previously obtained, were put together to obtain 9.2 g of 2,6-dichloro-4-trifluoromethyl-3-pyridine carboxamide.

(2) 9.2 g of 2,6-dichloro-4-trifluoromethyl-3-pyridine carboxamide obtained in the above step (1), 0.66 g of 10% palladium carbon and 6.4 g of anhydrous sodium acetate were added to 200 ml of methanol. Then, a reduction reaction was conducted under a hydrogen pressure at room temperature for 12 hours. After completion of the reaction, the reducing catalyst was removed by Celite, and the filtrate was concentrated. Extraction was conducted by adding ethyl acetate and water to the residue. The organic layer was dried over anhydrous sodium sulfate. Then, the solvent was distilled off to obtain 5.2 g of 4-trifluoromethyl-3-pyridine carboxamide as the desired product.

SYNTHESIS EXAMPLE 5

Preparation of ethyl 4-trifluoromethylnicotinoylaminoacetimidate (Compound No. 32)

Into an ice cooled kjeldahl type flask, 5 ml of absolute ethanol was added, and 100 mg (0.4 mmol) of 4-trifluoromethyl-N-(cyanomethlyl)-3-pyridine carboxamide was added thereto. After permitting the mixture to absorb hydrogen chloride, the flask was sealed and left to stand in a refrigerator for 21 hours. Then, the mixture was returned to room temperature and subjected to distillation under reduced pressure, followed by vacuum drying.

The hydrochloride thus obtained was added to an aqueous sodium hydrogen carbonate solution and thereby neutralized. Then, it was extracted with diethyl ether. The organic layer was dried over anhydrous sodium sulfate and concentrated under reduced pressure. The obtained residue was purified by silica gel column chromatography (developing solvent: n-hexane/ethyl acetate=3/7) to obtain 0.165 g (yield: 45.8%) of ethyl 4-trifluoromethylnicotinoylamide acetimidate having a melting point of from 64.5° to 66.0° C.

SYNTHESIS EXAMPLE 6

Preparation of O-methyl N-(4-trifluoromethylnicotinoyl thiocarbamate (Compound No. 9)

Into 30 ml of benzene, 1.12 g (11 mmol) of potassium thiocyanate was added, and 2.19 g (10 mmol) of 4-trifluoromethylnicotinic acid chloride was dropwise added thereto at room temperature. Then, the mixture was refluxed under heating for further 6 hours. After refluxing under heating, the mixture was distilled under reduced pressure to obtain 4-trifluoromethylnicotinyl thioisocyanate.

The thioisocyanate thus obtained was added into 30 ml of acetonitrile, and 0.44 ml (10.5 mmol) of methanol was dropwise added thereto at 0° C. The mixture was stirred at room temperature for 16 hours. The reaction solution was poured into water and extracted with ethyl acetate. The organic layer was washed with a saturated sodium chloride aqueous solution and then concentrated under reduced pressure. The residue thereby obtained was purified by silica gel column chromatography (developing solvent: n-hexane/ethyl acetate=6/4) to obtain 0.84 g (yield: 30.4%) of O-methyl N-(4-trifluoromethylnicotinoyl)thiocarbamate having a melting point of from 138° to 141.5° C.

SYNTHESIS EXAMPLE 7

Preparation of O-methyl S-methyl N-(4trifluoronicotinoyl)iminothiocarbonate (Compound No. 14)

Into a solution comprising 0.200 g (0.76 mmol) of O-methyl N-(4-trifluoromethylnicotinoyl)thiocarbamate obtained in the above Synthesis Example 6 and 2 ml of dimethylformamide, 0.034 g (0.85 mmol) of 60% sodium hydride was added at room temperature. The mixture was stirred for 15 minutes, and then 0.118 g (0.83 mmol) of methyl iodide was dropwise added thereto. The mixture was stirred at room temperature for one hour, then poured into water and extracted with ethyl acetate. The organic layer was washed with a saturated sodium chloride aqueous solution, dried over anhydrous sodium sulfate and concentrated under reduced pressure. The residue thereby obtained was purified by silica gel column chromatography (developing solvent: n-hexane/ethyl acetate=7/3) to obtain 0.133 g (yield: 63.1%) of oily O-methyl S-methyl N-(4-trifluoromethylnicotinoyl)iminocarbonate.

SYNTHESIS EXAMPLE 8

Preparation of N-(N'-isopropylaminomethyl)-4-trifluoromethylpyridine-3-carboxamide (Compound No. 4)

Into 30 ml of dimethoxyethane, 0.6 g of hydrogen chloride gas was blown at 20° C. Then, this solution was cooled to −30° C. Then, a solution having 0.72 g (3.4 mmol) of 1,3,5-triisopropyl-2,4,6-hexahydrotriazine dissolved in 5 ml of dimethoxyethane, was dropwise added thereto, and 1.88 g (9.9 mmol) of 4-trifluoromethylpyridine-3-carboxamide was further added thereto.

This solution was stirred at room temperature for 12 hours. Then, the solvent was distilled off under reduced pressure. The residue was dissolved in 30 ml of methanol, and then 3 g (30 mmol) of triethylamine was added thereto. Methanol was distilled off under reduced pressure, and then 30 ml of ethyl acetate was added thereto. Then, impurities were filtered off, and the filtrate was concentrated and purified by silica gel column chromatography (eluent: ethyl acetate/ethanol=85/15) to obtain 1.1 g (yield: 42.6%) of N-(N'-isopropylaminomethyl)-4-trifluoromethylpyridine-3-carboxamide having a melting point of 119.8° C., as the desired product.

SYNTHESIS EXAMPLE 9

Preparation of N-(N',N'-dimethylaminomethyl)-4-trifluoromethylpyridine-3-carboxamide (Compound No. 11)

To a mixed solution comprising 1.3 g (6.8 mmol) of 4-trifluoromethylpyridine-3-carboxamide, 1.5 ml of water and 0.63 g (7 mmol) of dimethylamine, 0.57 g (7 mmol) of a 37% formaldehyde aqueous solution was added. Then, the mixture was reacted at 80° C. for two hours. After completion of the reaction, anhydrous sodium carbonate was added to the reaction solution until it was saturated. Then, methylene chloride and water were added thereto, and extraction was conducted. The organic layer was dried over anhydrous sodium sulfate, and then the solvent was distilled off under reduced pressure. The residue thereby obtained was purified by silica gel column chromatography (eluent: ethyl acetate/methanol=19/1) to obtain 0.55 g (yield: 32.5%) of N-(N',N'-dimethylaminomethyl)-4-trifluoromethylpyridine-3-carboxamide (melting point: 50°–58° C.) as the desired product.

SYNTHESIS EXAMPLE 10

Preparation of 4-trifluoromethyl-3-pyridine carboxamide 1-oxide (Compound No. 11)

0.8 g of 4-trifluoromethyl-3-pyridine carboxamide was dissolved in 7 ml of acetic acid. Then, 0.72 g of a 30% hydrogen peroxide aqueous solution was gradually dropwise added thereto. After completion of the dropwise addition, the reaction solution was heated to 70° C. and stirred for 8 hours at this temperature. After completion of the reaction, the solvent was distilled off under reduced pressure. The residue thereby obtained was washed with n-hexane to obtain 0.6 g of 4-trifluoromethyl-3-pyridine carboxamide 1-oxide (melting point: 198.8° C.) as the desired product.

The compounds of the formula (I') produced by the present invention will be given in Table 1.

TABLE 1

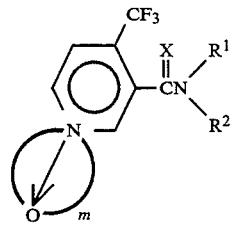

(I')

| Compound No. | X | R¹ | R² | m | Physical properties |
|---|---|---|---|---|---|
| 1 | O | —CH₂CN | H | 0 | mp. 155–161° C. |
| 2 | O | —CH₂CSNH₂ | H | 0 | mp. 190.5–193.5 |
| 3 | O | —CH₂OC₂H₅ | H | 0 | Amorphous solid |
| 4 | O | —CH₂NH—C₃H₇(i) | H | 0 | mp. 119.8° C. |
| 5 | O | H | H | 0 | mp. 162.7° C. |
| 6 | O | —CH₂CN | 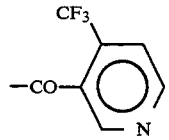 | 0 | mp. 116–123° C. |

TABLE 1-continued (I')

| Compound No. | X | R¹ | R² | m | Physical properties |
|---|---|---|---|---|---|
| 7 | O | —CH₂CN | —COCH₃ | 0 | Oil |
| 8 | O | —CH₂CN | —CH₃ | 0 | $n_D^{19.2}$ 1.4883 |
| 9 | O | —C(S)OCH₃ | H | 0 | mp. 138–141.5° C. |
| 10 | O | —CH₃ | H | 0 | mp. 83–89° C. |
| 11 | O | —CH₂N(CH₃)₂ | H | 0 | mp. 50–58° C. |
| 12 | O | —CH₂—N(piperidine) | H | 0 | mp. 195–200° C. |
| 13 | O | —CH₂CN | —CH₂OC(O)C(CH₃)₃ | 0 | Oil |
| 14 | O | =C(OCH₃)(SCH₃) | | 0 | Oil |
| 15 | O | —CH₂OH | H | 0 | mp. 105–113° C. |
| 16 | O | —COCH₃ | H | 0 | mp. 114–119° C. |
| 17 | O | —CO₂CH₃ | H | 0 | mp. 118–128° C. |
| 18 | O | —CH₂—C₆H₄—CF₃ | H | 0 | mp. 145–148° C. |
| 19 | O | —CH₂—C₆H₄—O—C₆H₄—SCH₃ | H | 0 | mp. 103–106° C. |
| 20 | O | —CH₂—C₆H₄—CF₃ | H | 0 | mp. 76.5–78.5° C. |
| 21 | O | —CH₂—C≡CH | H | 0 | mp. 108.5–109.5° C. |
| 22 | O | —CH₂CH=CH₂ | H | 0 | mp. 75.5–77° C. |
| 23 | O | —CH₂CH₂—C₆H₅ | H | 0 | mp. 110–111° C. |
| 24 | O | —CH₂CH₂OCH₃ | H | 0 | mp. 56.6–59° C. |
| 25 | O | —CH₂CH₂CH₂CH₃ | H | 0 | mp. 47.7° C. |
| 26 | O | Cyclopropyl | H | 0 | mp. 105.1° C. |
| 27 | O | —CH₂CH(CH₃)₂ | H | 0 | mp. 90.6° C. |
| 28 | O | —CH₂-cyclopropyl | H | 0 | mp. 90.6° C. |
| 29 | O | —CH₂CH₂CN | H | 0 | mp. 93.1° C. |
| 30 | O | —CH₂CONH₂ | H | 0 | mp. 155–158.5° C. |
| 31 | O | —CH₂SCH₃ | H | 0 | mp. 106.4° C. |

TABLE 1-continued

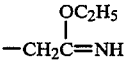

(I')

| Compound No. | X | R¹ | R² | m | Physical properties |
|---|---|---|---|---|---|
| 32 | O | —CH₂C(OC₂H₅)=NH | H | 0 | mp. 64.5–66° C. |
| 33 | O | —CH₂OC₂H₅ | —CH₂OC₂H₅ | 0 | $n_D^{22.4}$ 1.4648 |
| 34 | O | —CH₂CN | —CO₂CH₃ | 0 | Oil |
| 35 | O | —CH₃ | —CH₃ | 0 | $n_D^{22.0}$ 1.4717 |
| 36 | O | —CH₂CH(OH)CH₃ | H | 0 | mp. 94.9° C. |
| 37 | O | —CH₂CH₂OH | H | 0 | mp. 101.5° C. |
| 38 | O | —CH₂CO₂CH₃ | H | 0 | mp. 77.9° C. |
| 39 | O | —CH₂COCH₃ | H | 0 | mp. 112.7° C. |
| 40 | O | —CH₂CO—C₆H₅ | H | 0 | mp. 144.2° C. |
| 41 | O | —CH₂C≡CCH₂CH₃ | H | 0 | mp. 87.9° C. |
| 42 | O | —CH(CH₃)—C₆H₄—Cl | H | 0 | mp. 107–112° C. |
| 43 | O | —CH₂CH(OC₂H₅)₂ | H | 0 | mp. 73–77° C. |
| 44 | O | —CH₂CN | —CH₂OCH₃ | 0 | Oil |
| 45 | O | —CH₂CN | —SO₂CH₃ | 0 | Oil |
| 46 | O | —C(S)SC₂H₅ | H | 0 | mp. 83–85° C. |
| 47 | O | =C(SC₂H₅)(SC₂H₅) | | 0 | mp. 30–33° C. |
| 48 | O | =C(OCH₃)(SC₂H₅) | | 0 | mp. 30–32° C. |
| 49 | O | —CO₂CH₃ | —CO₂CH₃ | 0 | mp. 67–87° C. |
| 50 | O | —CH₂CHO | H | 0 | Amorphous solid |
| 51 | O | =C(SC₂H₅)(SC₂H₅) | | 0 | mp. 46.5–48.0° C. |
| 52 | O | —CH₂—C₆H₄—Cl (2-Cl) | H | 0 | mp. 123–124° C. |
| 53 | O | —CH₂—C₆H₄—Cl (4-Cl) | H | 0 | mp. 161–163° C. |
| 54 | O | —CH₂—C₆H₄—Cl (3-Cl) | H | 0 | mp. 105.5–108° C. |

TABLE 1-continued (I')

structure: pyridine with CF$_3$ substituent, X=C-NR$^1$R$^2$ group, and N-CH$_2$-O bridge (m)

| Compound No. | X | R$^1$ | R$^2$ | m | Physical properties |
|---|---|---|---|---|---|
| 55 | O | -CH$_2$-(2-CH$_3$O-C$_6$H$_4$) | H | 0 | mp. 119.5–123.5° C. |
| 56 | O | -CH$_2$-(4-OCH$_3$-C$_6$H$_4$) | H | 0 | mp. 140.5–143° C. |
| 57 | O | -CH$_2$-(4-NO$_2$-C$_6$H$_4$) | H | 0 | mp. 165–169° C. |
| 58 | O | -CH$_2$-(4-C(CH$_3$)$_3$-C$_6$H$_4$) | H | 0 | mp. 65–67° C. |
| 59 | O | -CH$_2$-(2-NO$_2$-C$_6$H$_4$) | H | 0 | mp. 127–133° C. |
| 60 | O | -CH$_2$-(2-CH$_3$-C$_6$H$_4$) | H | 0 | mp. 130–132° C. |
| 61 | O | -CH$_2$-(3-CH$_3$-C$_6$H$_4$) | H | 0 | mp. 92–94° C. |
| 62 | O | -CH$_2$-(2-CF$_3$-C$_6$H$_4$) | H | 0 | mp. 115.5–117° C. |
| 63 | O | -CH$_2$CH$_2$N(CH$_3$)$_2$ | H | 0 | mp. 94.5–96.5° C. |
| 64 | O | -CH$_2$CH$_3$ | H | 0 | mp. 85–86° C. |
| 65 | O | -CH$_2$CH$_2$-N(piperidinyl) | H | 0 | mp. 82–83° C. |

TABLE 1-continued (I')

[Structure: pyridine with CF3 substituent, C(=X)NR¹R² group, and N-CH-O bridged ring with subscript m]

| Compound No. | X | R¹ | R² | m | Physical properties |
|---|---|---|---|---|---|
| 66 | O | —CH₂CH₂—O—(phenyl) | H | 0 | mp. 112–113.3° C. |
| 67 | O | —NH—(2-pyridyl) | H | 0 | mp. 186–188° C. |
| 68 | O | —CH(CH₂CH₃)CN | H | 0 | Oil |
| 69 | O | Cyclopentyl | H | 0 | mp. 115.0° C. |
| 70 | O | Cyclohexyl | H | 0 | mp. 112.4° C. |
| 71 | O | —CH₂C(CH₃)₃ | H | 0 | mp. 87.7° C. |
| 72 | O | —CH₂C(NH₂)=NH | H | 0 | mp. 166–169° C. |
| 73 | O | —CH₂CONHC(CH₃)₃ | H | 0 | mp. 158–160° C. |
| 74 | O | —CH₂SO₂CH₃ | H | 0 | mp. 198–203° C. |
| 75 | O | —CH₂CH₂OC(O)-(4-CF₃-2-pyridyl) | H | 0 | mp. 121.2° C. |
| 76 | O | —CH₂CH(OCH₃)₂ | H | 0 | mp. 123.1° C. |
| 77 | O | —CH₂CH₂CH₂C≡CH | H | 0 | mp. 73.0° C. |
| 78 | O | —CH₂CH=C(CH₃)₂ | H | 0 | mp. 62–66° C. |
| 79 | O | —CH₂CH₂—O—CH₂CH₂— | | 0 | $n_D^{14.8}$ 1.4922 |
| 80 | O | —CH₂CH₂—N(CH₃)—CH₂CH₂— | | 0 | $n_D^{21.0}$ 1.4476 |
| 81 | O | —CH₂-(4-methylphenyl) | H | 0 | mp. 143–146° C. |
| 82 | O | —CH₂CF₃ | H | 0 | mp. 119.5–121° C. |
| 83 | O | —C(CH₃)(CO₂CH₃)CH(CH₃)₂ | H | 0 | mp. 115–116° C. |
| 84 | O | —C(CH₃)₃ | H | 0 | mp. 104.8° C. |
| 85 | O | —CH₂N(pyrrolidinyl) | H | 0 | mp. 107–110° C. |
| 86 | O | —CH₂N(morpholinyl) | H | 0 | mp. 143–146° C. |

TABLE 1-continued (I')

[Structure: pyridine ring with CF₃ substituent and C(=X)NR¹R² group, with O linker, subscript m]

| Compound No. | X | R¹ | R² | m | Physical properties |
|---|---|---|---|---|---|
| 87 | O | −CH₂N(piperazine)N−CH₃ | H | 0 | mp. 155–157° C. |
| 88 | O | −CH₂−N(2,6-dimethylmorpholine) | H | 0 | mp. 166–171° C. |
| 89 | S | H | H | 0 | mp. 143–147° C. |
| 90 | S | −CH₂CN | H | 0 | — |
| 91 | O | −CH₂N(piperazine)N−phenyl | H | 0 | mp. 142–146° C. |
| 92 | O | −CH₂N(pyrrolidine) | −CH₃ | 0 | |
| 93 | O | −CH₂N(piperidine) | −C₂H₅ | 0 | |
| 94 | O | −CH₂N(CH₃)₂ | −CH₃ | 0 | |
| 95 | O | −CH₂Si(CH₃)₃ | H | 0 | |
| 96 | O | −CH₂N(piperazine)N−(2-pyridyl) | H | 0 | |
| 97 | O | −CH₂N(piperazine)N−(4-CF₃-2-pyridyl) | H | 0 | |
| 98 | O | −CH₂N(piperazine)N−CH₃ | −CH₃ | 0 | |
| 99 | O | −CH₂CH₂NHCO−(4-CF₃-pyridin-3-yl) | H | 0 | mp. 271–275° C. |

TABLE 1-continued (I')

| Compound No. | X | R¹ | R² | m | Physical properties |
|---|---|---|---|---|---|
| 100 | O | —CH₂CH₂NCO—[4-CF₃-pyridin-2-yl] with N-CH₃ | —CH₃ | 0 | |
| 101 | O | —CH₂CH₂OCH₂CH₂NCO—[4-CF₃-pyridin-2-yl] with N-H | H | 0 | |
| 102 | O | —SO₂CH₃ | H | 0 | 67–75° C. (amorphous) |
| 103 | O | —CH₂OCOC(CH₃)₃ | H | 0 | 142–145° C. |
| 104 | O | —COCH₃ | COCH₃ | 0 | mp. 68–72° C. |
| 105 | O | —SO₂N(CH₃)₂ | H | 0 | mp. 172–174° C. |
| 106 | O | —CONHCH₃ | H | 0 | mp. 161–164.5° C. |
| 107 | O | —CH₃ | —COCH₃ | 0 | mp. 49–51° C. |
| 108 | O | —CH₃ | —CO₂CH₃ | 0 | mp. 44–46° C. |
| 109 | O | —CH₂SCH₃ | —CH₂SCH₃ | 0 | $n_D^{22.4}$ 1.5344 |
| 110 | O | —C(=N—CN)—N(CH₃)—CH₂—CH₂— (cyclic) | | 0 | mp. 160–163° C. |
| 111 | O | H | H | 1 | mp. 198.8° C. |
| 112 | O | —CH₃ | H | 1 | mp. 119–127° C. |
| 113 | O | —CH₂CH₃ | H | 1 | |
| 114 | O | —CH₂CN | H | 1 | mp. 155–156.5° C. |
| 115 | O | —CH₂N(piperidinyl) | H | 1 | |
| 116 | O | —CH₂N(pyrrolidinyl) | H | 1 | |
| 117 | O | —COCH₃ | H | 1 | |
| 118 | O | —CH₂CH=CH₂ | H | 1 | |
| 119 | O | —CH₂—C≡CH | H | 1 | |
| 120 | O | —CH₂CSNH₂ | H | 1 | |
| 121 | O | —CH₂NHCH₃ | H | 1 | |
| 122 | O | —CH₂OH | H | 1 | |
| 123 | S | H | H | 1 | |

The compounds of the formula (I) also include the following compounds.

Compound No. 124; 4-chlorodifluoromethyl-3-pyridine carboxamide

Compound No. 125; 4-dichlorofluoromethyl-3-pyridine carboxamide

Compound No. 126; 4-trichloromethyl-3-pyridine carboxamide

Compound No. 127; 4-difluoromethyl-3-pyridine carboxamide

Compound No. 128; 4-fluoromethyl-3-pyridine carboxamide

Compound No. 129; 4-β,β,β-trifluoroethyl-3-pyridine carboxamide

Compound No. 130; 4-pentafluoroethyl-3-pyridine carboxamide

Compound No. 131; 4-dibromomethyl-3-pyridine carboxamide (mp. 115°-17.5° C.)

Compound No. 132; 4-bromomethyl-3-pyridine carboxamide

TEST EXAMPLE 1

Insecticidal test against green peach aphid (*Myzus persicae*)

Each formulation containing an active ingredient was dispersed in water to obtain a dispersion of each active ingredient having a concentration of 800 ppm. The petiole of each of eggplants with only one foliage leaf left(planted in a pot having a diameter of 8 cm and a height of 7 cm) was coated with a sticker, and about 2-3 apterous viviparous female of green peach aphid (*Myzus persicae*) were infested and incubated on the foliage leaf of the eggplant. After two days from the infestation, the adult insects were removed and the number of larvae was counted. Then, the foliage leaf of the eggplant infested with the larvae was dipped in the above prepared dispersion having the predetermined concentration for about 10 seconds, then dried in air and kept in a constant temperature chamber with lightening at 26° C. On the 5th day after the treatment, dead insects were counted, and the mortality was calculated by the following equation:

$$\text{Mortality (\%)} = \frac{\text{Number of dead insects}}{\text{Number of treated insects}} \times 100$$

The insects released from the leaf were counted as dead insects.

As a result, the mortality was 100% with each of Compounds Nos. 1-56, 58-66, 69, 70, 72-79, 82, 85-89, 91, 99 and 102-111, and from 90 to 99% with each of Compounds Nos. 57, 67, 68, 71 and 80.

TEST EXAMPLE 2

Systemic test against green peach aphid (*Myzus Persicae*)

Each of formulation containing an active ingredient was dispersed in water to obtain a dispersion of each active ingredient having a concentration of 800 ppm. The petiole of each of eggplants with only one foliage leaf left (planted in a pot having a diameter of 8 cm and a height of 7 cm) was coated with a sticker, and about 2-3 apterous viviparous female of green peach aphid (*Myzus Persicae*) were infested and incubated to the foliage leaf of the eggplant. After two days from the infestation, the adult insects were removed and the number of larvae was counted. Then, the eggplant infested with the larvae was treated by drenching 10 ml of the above prepared dispersion having the predetermined concentration into the soil in the pot, and was kept in a constant temperature chamber with lightening at 26° C. On the 5th day after the treatment, dead insects were counted, and the mortality was calculated in the same manner as in Test Example 1.

As a result, the mortality was 100% with each of Compounds Nos. 1-17, 20-23, 26-28, 30, 31, 33-37, 39-41, 44, 46, 49, 50, 78, 85, 86, 88, 89, 99, 103, 104 and 111.

TEST EXAMPLE 3

Systemic test against *Thrips palmi*

Each of formulation containing an active ingredient was dispersed in water to obtain a dispersion of each active ingredient having a concentration of 800 ppm. The petiole of each of eggplants with only one foliage leaf left (planted in a pot having a diameter of 8 cm and a height of 7 cm) was coated with a sticker, and about 20 adult insects of *Thrips palmi* were infested to the foliage leaf of the eggplant. After one day from the infestation, the eggplant infested with the adult insects was treated by drenching 10 ml of the above prepared dispersion having the predetermined concentration into the soil in the pot, and was kept in a constant temperature chamber with lightening at 26° C. On the 8th day after the treatment, the number of the parasitic adult insects and larvae of the next generation was counted.

On a non-treated eggplant, 4 adult insects and 172 larvae were parasitic. Whereas, on the eggplants treated with Compounds Nos. 1, 5 and 85, no adult insects or larvae were observed, thus indicating high insecticidal effects.

Now, the Formulation Examples of the present invention will be given. However, the compounds of the present invention, the amounts of the active ingredients or the types of the formulations-are not restricted to these specific Examples.

FORMULATION EXAMPLE 1

| (a) Compound No. 1 | 20 parts by weight |
| (b) Kaoline | 72 parts by weight |
| (c) Sodium lignin sulfonate | 8 parts by weight |

The above components are uniformly mixed to obtain a wettable powder.

FORMULATION EXAMPLE 2

| (a) Compound No. 4 | 5 parts by weight |
| (b) Talc | 95 parts by weight |

The above components are uniformly mixed to obtain a dust.

FORMULATION EXAMPLE 3

| (a) Compound No. 2 | 20 parts by weight |
| (b) N,N'-dimethylacetamide | 20 parts by weight |
| (c) Polyoxyethylenealkylphenyl ether | 10 parts by weight |
| (d) Xylene | 50 parts by weight |

The above components are uniformly mixed and dissolved to obtain an emulsifiable concentrate.

FORMULATION EXAMPLE 4

| (a) Kaoline | 68 parts by weight |
| (b) Sodium lignin sulfonate | 2 parts by weight |
| (c) Polyoxyethylenealkylaryl sulfate | 5 parts by weight |
| (d) Fine silica powder | 25 parts by weight |

A mixture of the above Components is mixed with Compound No. 5 in a weight ratio of 4:1 to obtain a wettable powder.

FORMULATION EXAMPLE 5

| (a) Compound No. 12 | 50 parts by weight |
| (b) Oxylated polyalkylphenyl phosphate-triethanolamine | 2 parts by weight |

| | |
|---|---|
| (c) Silicone | 0.2 part by weight |
| (d) Water | 47.8 parts by weight |

The above components are uniformly mixed and pulverized to obtain a base liquid, and

| | |
|---|---|
| (e) Sodium polycarboxylate | 5 parts by weight |
| (f) Anhydrous sodium sulfate | 42.8 parts by weight | are added, and the mixture is uniformly mixed and dried to obtain a water dispersible granules.

FORMULATION EXAMPLE 6

| | |
|---|---|
| (a) Compound No. 85 | 5 parts by weight |
| (b) Polyoxyethyleneoctylphenyl ether | 1 part by weight |
| (c) Phosphoric acid ester of poly-oxyethylene | 0.5 part by weight |
| (d) Granular calcium carbonate | 93.5 parts by weight |

The above components (a) to (c) are uniformly mixed and kneaded together with a small amount of acetone, and then the mixture is sprayed onto the component (d) to remove acetone, thus obtaining granules.

FORMULATION EXAMPLE 7

| | |
|---|---|
| (a) Compound No. 16 | 2.5 parts by weight |
| (b) N-methyl-2-pyrrolidone | 2.5 parts by weight |
| (c) Soybean oil | 95.0 parts by weight |

The above components are uniformly mixed and dissolved to obtain an ultra low-volume formulation.

FORMULATION EXAMPLE 8

| | |
|---|---|
| (a) Compound No. 3 | 5 parts by weight |
| (b) N,N'-dimethylacetamide | 15 parts by weight |
| (c) Polyoxyethylenealkyl aryl ether | 10 parts by weight |
| (d) Xylene | 70 parts by weight |

The above components are uniformly mixed to obtain an emulsifiable concentrate.

FORMULATION EXAMPLE 9

| | |
|---|---|
| (a) Compound No. 111 | 20 parts by weight |
| (b) Sodium laurylsulfate | 3 parts by weight |
| (c) Water-soluble starch | 77 parts by weight |

The above components are uniformly mixed to obtain a water soluble powder.

We claim:

1. An amide compound of the formula (I) or its salt:

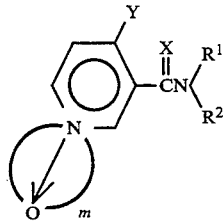
(I)

wherein X is an oxygen atom or a sulfur atom, Y is a haloalkyl group, each of $R^1$ and $R^2$ which are independent of each other, is a hydrogen atom, an alkyl group which may be substituted, an alkenyl group which may be substituted, an alkynyl group which may be substituted, a cycloalkyl group which may be substituted, $-C(W^1)R^3$, $-S(O)_nR^4$ or $-NHR^5$, or $R^1$ and $R^2$ together form $=C(R^6)R^7$ or together with the adjacent nitrogen atom form a 5- or 6-member heterocyclic group which may contain a nitrogen atom or an oxygen atom, $R^3$ is an alkyl group which may be substituted, an alkenyl group which may be substituted, an alkynyl group which may be substituted, a cycloalkyl group which may be substituted, an aryl group which may be substituted, an alkoxy group, an alkylthio group or a mono- or di-alkylamino group, $R^4$ is an alkyl group or a dialkylamino group, $R^5$ is an alkyl group or an aryl group, each of $R^6$ and $R^7$ which are independent of each other, is an alkoxy group or an alkylthio group, $W^1$ is an oxygen atom or a sulfur atom, m is 0 or 1, and n is 1 or 2, provided that when m is 0 and X is an oxygen atom and Y is a trifluoromethyl or a dibromomethyl group, $R^1$ and $R^2$ are not simultaneously hydrogen atoms;

wherein the substituent for the alkyl group which may be substituted, the alkenyl group which may be substituted, the alkynyl group which may be substituted or the cycloalkyl group which may be substituted in the definition of each of $R^1$, $R^2$ and $R^3$ in the formula (I), is a halogen atom; alkoxy; alkylthio; trialkylsilyl; phenyl; phenyl substituted by halogen, alkyl, alkoxy, nitro or haloalkyl; phenyl substituted by phenoxy which may be substituted by alkoxy or alkylthio; phenoxy; phenylthio; amino; amino substituted by one or two alkyl; cyclic amino; morpholino; morpholino substituted by alkyl; 1-piperazinyl; 1-piperazinyl substituted by alkyl, phenyl, pyridyl or trifluoromethylpyridyl; hydroxy; cyano; cycloalkyl; imino; $-C(W^2)R^8$, wherein $W^2$ is an oxygen atom or a sulfur atom, and $R^8$ is a hydrogen atom, amino, amino substituted by one or two alkyl, alkyl, alkoxy, alkylthio or aryl; $-OC(W^2)R^9$, wherein $R^9$ is alkyl or aryl substituted by haloalkyl; or an alkylsulfonyl; and when the substituent is an imino group, it can form an amidino group or an imidate group together with an amino group or an alkoxy group; and the substituent for the aryl group which may be substituted in the definition for $R^3$ in the formula (I), is a halogen atom, alkyl, haloalkyl, alkoxy, haloalkoxy, alkylthio, cycloalkyl, cycloalkoxy, alkoxycarbonyl, alkylcarbonyl, alkylcarbonyloxy, aryl, aryloxy, arylthio, amino, amino substituted by one or two alkyl, cyano, nitro or hydroxy.

2. An amide compound of the formula (I') or its salt:

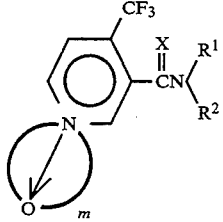
(I')

wherein X is an oxygen atom or a sulfur atom, each of $R^1$ and $R^2$ which are independent of each other, is a hydrogen atom, an alkyl group which may be substituted, an alkenyl group which may be substituted, an alkynyl group which may be substituted, a cycloalkyl group which may be substituted, —C(W¹)R³, —S-(O)ₙR⁴ or —NHR⁵, or R¹ and R² together form =C(R⁶)R⁷ or together with the adjacent nitrogen atom form a 5- or 6-member heterocyclic group which may contain a nitrogen atom or an oxygen atom, R³ is an alkyl group which may be substituted, an alkenyl group which may be substituted, an alkynyl group which may be substituted, a cycloalkyl group which may be substituted, an aryl group which may be substituted, an alkoxy group, an alkylthio group or a mono- or di-alkylamino group, R⁴ is an alkyl group or a dialkylamino group, R⁵ is an alkyl group or an aryl group, each of R⁶ and R⁷ which are independent of each other, is an alkoxy group or an alkylthio group, W¹ is an oxygen atom or a sulfur atom, m is 0 or 1, and n is 1 or 2, provided that when m is 0 and X is an oxygen atom, R¹ and R² are not simultaneously hydrogen atoms;

wherein the substituent for the alkyl group which may be substituted, the alkenyl group which may be substituted, the alkynyl group which may be substituted or the cycloalkyl group which may be substituted in the definition of each of R¹, R² and R³ is a halogen atom; alkoxy; alkylthio; trialkylsilyl; phenyl; phenyl substituted by halogen, alkyl, alkoxy, nitro or haloalkyl; phenyl substituted by phenoxy which may be substituted by alkoxy or alkylthio; phenoxy; phenylthio; amino; amino substituted by one or two alkyl; cyclic amino; morpholino; morpholino substituted by alkyl; 1-piperazinyl; 1-piperazinyl substituted by alkyl, phenyl, pyridyl or trifluoromethylpyridyl; hydroxy; cyano; cycloalkyl; imino; —C(W²)R⁸, wherein W² is an oxygen atom or a sulfur atom, and R⁸ is a hydrogen atom, amino, amino substituted by one or two alkyl, alkyl, alkylthio or aryl; —OC(W²)R⁹, wherein R⁹ is alkyl or aryl substituted by haloalkyl; or an alkylsulfonyl; and when the substituent is an imino group, it can form an amidino group or an imidate group together with an amino group or an alkoxy group; and the substituent for the aryl group which may be substituted in the definition for R³ is a halogen atom, alkyl, haloalkyl, alkoxy, haloalkoxy, alkylthio, cycloalkyl, cycloalkoxy, alkoxycarbonyl, alkylcarbonyl, alkylcarbonyloxy, aryl, aryloxy, arylthio, amino, amino substituted by one or two alkyl, cyano, nitro or hydroxy.

3. The compound of the formula (I') or its salt according to claim 2, wherein X is an oxygen atom.

4. The compound of the formula (I') or its salt according to claim 2, wherein each of R¹ and R² which are independent of each other, is a hydrogen atom, an alkyl group which may be substituted, or —C(W¹)R³, or R¹ and R² together form =C(R⁶)R⁷, W¹ is an oxygen atom or a sulfur atom, R³ is an alkyl group which may be substituted, an aryl group which may be substituted, or an alkoxy group, and each of R⁶ and R⁷ which are independent of each other, is an alkoxy group or an alkylthio group.

5. The compound of the formula (I') or its salt according to claim 2, wherein X is an oxygen atom, each of R¹ and R² which are independent of each other, is a hydrogen atom, an alkyl group, an alkoxyalkyl group, an alkylaminoalkyl group, a cyclic aminoalkyl group, a hydroxyalkyl group, a cyanoalkyl group, a thiocarbamoylalkyl group, an alkylcarbonyloxyalkyl group, an alkylcarbonyl group, an arylcarbonyl group, a trifluoromethyl-substituted arylcarbonyl group, an alkoxythiocarbonyl group or an alkoxycarbonyl group, or R¹ and R² together form =C(R⁶)R⁷, and R⁶ and R⁷ are an alkoxy group and and alkylthio group, respectively.

6. The compound of the formula (I') or its salt according to claim 2, wherein said compound is 4-trifluoromethyl-3-pyridinecarboxamide 1-oxide; or N-cyanomethyl-4-trifluoromethyl-3-pyridine carboxamide, N-thiocarbamoylmethyl-4-trifluoromethyl-3-pyridine carboxamide, N-ethoxymethyl-4-trifluoromethyl-3-pyridine carboxamide, N-isopropylaminomethyl-4-trifluoromethyl-3-pyridine carboxamide, N-cyanomethyl-N,N-bis(4-trifluoromethylnicotinoyl)amine, N-acetyl-N-cyanomethyl-4-trifluoromethyl-3-pyridine carboxamide, N-cyanomethyl-N-methyl-4-trifluoromethylpyridine-3-carboxamide, O-methyl N-(4-trifluoromethylnicotinoyl)thiocarbamate, N-methyl-4-trifluoromethylpyridine-3-carboxamide, N-(N',N'-dimethylaminomethyl)-4-trifluoromethylpyridine-3-carboxamide, N-(1-piperidinylmethyl)-4-trifluoromethylpyridine-3-carboxamide, N-cyanomethyl N-(4-trifluoromethylnicotinoyl)aminomethylpivarate, O,S-dimethyl N-(4-trifluoromethylnicotinoyl)iminoformate, N-hydroxymethyl-4-trifluoromethyl-3-pyridine carboxamide, N-acetyl-4-trifluoromethyl-3-pyridine carboxamide or methyl N-(4-trifluoromethylnicotinoyl)carbamate, or a 1-oxide thereof.

7. A pesticidal composition comprising a pesticidally effective amount of an amide compound of the formula (I) or its salt:

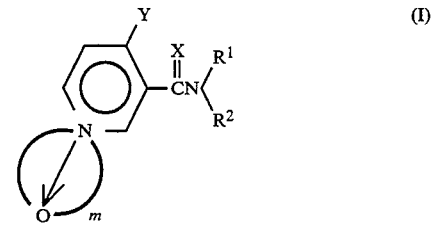

wherein X is an oxygen atom or a sulfur atom, Y is a haloalkyl group, each of R¹ and R² which are independent of each other, is a hydrogen atom, an alkyl group which may be substituted, an alkenyl group which may be substituted, an alkynyl group which may be substituted, a cycloalkyl group which may be substituted, —C(W¹)R³, —S(O)ₙR⁴ or —NHR⁵, or R¹ and R² together form =C(R⁶)R⁷ or together with the adjacent nitrogen atom form a 5- or 6-member heterocyclic group which may contain a nitrogen atom or an oxygen atom, R³ is an alkyl group which may be substituted, an alkenyl group which may be substituted, an alkynyl group which may be substituted, a cycloalkyl group which may be substituted, an aryl group which may be substituted, an alkoxy group, an alkylthio group or a mono- or di-alkylamino group, R⁴ is an alkyl group or a dialkylamino group, R⁵ is an alkyl group or an aryl group, each of R⁶ and R⁷ which are independent of each other, is an alkoxy group or an alkylthio group, W¹ is an oxygen atom or a sulfur atom, m is 0 or 1, and n is 1 or 2, wherein the substituent for the alkyl group which may be substituted, the alkenyl group which may be substituted, the alkynyl group which may be substituted or the cycloalkyl group which may be substituted in the definition of each of $R^1$, $R^2$ and $R^3$ in the formula (I), is a halogen atom; alkoxy; alkylthio; trialkylsilyl; phenyl; phenyl substituted by halogen, alkyl, alkoxy, nitro or haloalkyl; phenyl substituted by phenoxy which may be substituted by alkoxy or alkylthio; phenoxy; phenylthio; amino; amino substituted by one or two alkyl; cyclic amino; morpholino; morpholino substituted by alkyl; 1-piperazinyl; 1-piperazinyl substituted by alkyl, phenyl, pyridyl or trifluoromethylpyridyl; hydroxy; cyano; cycloalkyl; imino; —C($W^2$)$R^8$, wherein $W^2$ is an oxygen atom or a sulfur atom, and $R^8$ is a hydroge atom, amino, amino substituted by one or two alkyl, alkyl, alkoxy, alkylthio or aryl; —OC($W^2$)$R^9$, wherein $R^9$ is alkyl or aryl substituted by haloalkyl; or an alkylsulfonyl; and when the substituent is an imino group, it can form an amidino group or an imidate group together with an amino group or an alkoxy group; and the substituent for the aryl group which may be substituted in the definition for $R^3$ in the formula (I), is a halogen atom, alkyl, haloalkyl, alkoxy, haloalkoxy, alkylthio, cycloalkyl, cycloalkoxy, alkoxycarbonyl, alkylcarbonyl, alkylcarbonyloxy, aryl, aryloxy, arylthio, amino, amino substituted by one or two alkyl, cyano, nitro or hydroxy as an active ingredient, and an agricultural adjuvant.

8. A pesticidal composition comprising a pesticidally effective amount of an amide compound of the formula (I') or its salt:

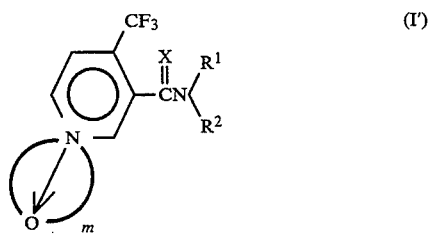

(I')

wherein X is an oxygen atom or a sulfur atom, each of $R^1$ and $R^2$ which are independent of each other, is a hydrogen atom, an alkyl group which may be substituted, an alkenyl group which may be substituted, an alkynyl group which may be substituted, a cycloalkyl group which may be substituted, —C($W^1$)$R^3$, —S(O)$_n R^4$ or —NHR$^5$, or $R^1$ and $R^2$ together form =C($R^6$)$R^7$ or together with the adjacent nitrogen atom form a 5- or 6-member heterocyclic group which may contain a nitrogen atom or an oxygen atom, $R^3$ is an alkyl group which may be substituted, an alkenyl group which may be substituted, an alkynyl group which may be substituted, a cycloalkyl group which may be substituted, an aryl group which may be substituted, an alkoxy group, an alkylthio group or a mono- or dialkylamino group, $R^4$ is an alkyl group or a dialkylamino group, $R^5$ is an alkyl group or an aryl group, each of $R^6$ and $R^7$ which are independent of each other, is an alkoxy group or an alkylthio group, $W^1$ is an oxygen atom or a sulfur atom, m is 0 or 1, and n is 1 or 2, wherein the substituent for the alkyl group which may be substituted, the alkenyl group which may be substituted, the alkylnyl group which may be substituted or the cycloalkyl group which may be substituted in the definition of each of $R^1$, $R^2$ and $R^3$ is a halogen atom; alkoxy; alkylthio; trialkylsilyl; phenyl; phenyl substituted by halogen, alkyl, alkoxy, nitro or haloalkyl; phenyl substituted by phenoxy which may be substituted by alkoxy or alkylthio; phenoxy; phenylthio; amino; amino substituted by one or two alkyl; 1-piperazinyl; 1-piperazinyl substituted by alkyl, phenyl, pyridyl or trifluoromethylpyridyl; hydroxy; cyano; cycloalkyl; imino; —C($W^2$)$R^8$, wherein $W^2$ is an oxygen atom or a sulfur atom, and $R^8$ is a hydrogen atom, amino, amino substituted by one or two alkyl, alkyl, alkoxy, alkylthio or aryl; —OC($W^2$)$R^9$, wherein $R^9$ is alkyl or aryl substituted by haloalkyl; or an alkylsulfonyl; and when the substituent is an imino group, it can form an amidino group or an imidate group together with an amino group or an alkoxy group; and the substituent for the aryl group which may be substituted in the definition for $R^3$ is a halogen atom, alkyl, haloalkyl, alkoxy, haloalkoxy, alkylthio, cycloalkyl, cycloalkoxy, alkoxycarbonyl, alkylcarbonyl, alkylcarbonyloxy, aryl, aryloxy, arylthio, amino, amino substituted by one or two alkyl, cyano, nitro or hydroxy as an active ingredient, and an agricultural adjuvant.

9. The pesticidal composition according to claim 8, wherein the active ingredient is 4-trifluoromethyl-3-pyridine carboxamide, N-cyanomethyl-4-trifluoromethyl-3-pyridine carboxamide, N-thiocarbamoylmethyl-4-trifluoromethyl-3-pyridine carboxamide, N-ethoxymethyl-4-trifluoromethyl-3-pyridine carboxamide, N-isopropylaminomethyl-4-trifluoromethyl-3-pyridine carboxamide, N-cyanomethyl -N,N-bis(4-trifluoromethylnicotinoyl)amine, N-acetyl-N-cyanomethyl-4-trifluoromethyl-3-pyridine carboxamide, N-cyanomethyl-N-methyl-4-trifluoromethylpyridine-3-carboxamide, O-methyl N-(4-trifluoromethylnicotinoyl)thiocarbamate, N-methyl-4-trifluoromethylpyridine-3-carboxamide, N-(N',N'-dimethylaminomethyl)-4-trifluoromethylpyridine-3-carboxamide, N-(1-piperidinyl)-4-trifluoromethylpyridine-3-carboxamide, N-cyanomethyl N-(4-trifluoromethylnicotinoyl)aminomethylpivarate, O,S-dimethyl N-(4-trifluoromethylnicotinoyl)iminoformate, N-hydroxymethyl-4-trifluoromethyl-3-pyridine carboxamide, N-acetyl-4-trifluoromethyl-3-pyridine carboxamide or methyl N-(4-trifluoromethylnicotinoyl)carbamate, or a 1-oxide thereof.

10. The pesticidal composition according to claim 8, wherein the active ingredient is 4-trifluoromethyl-3pyridine carboxamide or its 1-oxide.

11. A method for controlling a pest, which comprises applying an effective amount of an amide compound of the formula (I) or its salt as defined in claim 8 as an active ingredient to the pest.

12. The method according to claim 11, wherein the active ingredient is 4-trifluoromethyl-3-pyridine carboxamide or its 1-oxide.

* * * * *